US006932804B2

United States Patent
Lee

(10) Patent No.: US 6,932,804 B2
(45) Date of Patent: Aug. 23, 2005

(54) SYSTEM AND METHOD FOR FORMING A NON-ABLATIVE CARDIAC CONDUCTION BLOCK

(75) Inventor: Randall J. Lee, Hillsborough, CA (US)

(73) Assignee: The Regents of the University of California, Oakland, CA (US)

( * ) Notice: Subject to any disclaimer, the term of this patent is extended or adjusted under 35 U.S.C. 154(b) by 65 days.

(21) Appl. No.: 10/349,323

(22) Filed: Jan. 21, 2003

(65) Prior Publication Data

US 2004/0143238 A1 Jul. 22, 2004

(51) Int. Cl.$^7$ ............................................. A61M 31/00
(52) U.S. Cl. ................................................... 604/506
(58) Field of Search ............................ 604/65–67, 500, 604/510, 506, 511, 507, 514, 508, 57, 509, 515–522; 128/DIG. 12, DIG. 13; 607/3, 4, 5, 9, 13

(56) References Cited

U.S. PATENT DOCUMENTS

| 4,316,472 A | 2/1982 | Mirowski et al. |
| 4,354,497 A | 10/1982 | Kahn |
| 4,399,818 A | 8/1983 | Money |
| 4,565,200 A | 1/1986 | Cosman |
| 4,569,801 A | 2/1986 | Molloy et al. |
| 4,616,333 A | 10/1986 | Shimoni |
| 4,641,649 A | 2/1987 | Walinsky et al. |
| 4,660,571 A | 4/1987 | Hess et al. |
| 4,699,147 A | 10/1987 | Chilson et al. |
| 4,790,311 A | 12/1988 | Ruiz |
| 4,790,317 A | 12/1988 | Davies |
| 4,799,493 A | 1/1989 | DuFault |
| 4,807,620 A | 2/1989 | Strul et al. |
| 4,882,777 A | 11/1989 | Narula |

(Continued)

FOREIGN PATENT DOCUMENTS

| DE | 296 09 350 U1 | 10/1995 |
| DE | 195 37 084 A1 | 4/1997 |
| EP | 0 149 431 A2 | 7/1985 |

(Continued)

OTHER PUBLICATIONS

Sueda, Taijiro et al, Simple Left Atrial Procedure for Chronic Atrial Fibrillation Associated with Mitral Valve Disease; Ann Thorac Surg, Jun. 27, 1996; 62:1796–800.

Schueger, Claudio D. et al, Long–term Effects of Percutaneous Laser Balloon Ablation From the Canine Coronary Sinus; Circulation vol. 86, No. 3, Sep. 1992.

McMath, Linda P. et al, Percutaneous Laser Balloon Coagulation of Accessory Pathways; SPIE vol. 1425: 165–71 Diagnostic and Therapeutic Cardiovascular Interventions (1991).

Jais, MD, Pierre et al, Biatrial Dimensions Relevant to Catheter Ablation; North American Society of . . . ; 17th Annual Scientific Sessions Abstract Form; Nov. 28, 1995.

(Continued)

Primary Examiner—Manuel Mendez
(74) Attorney, Agent, or Firm—John P. O'Banion

(57) ABSTRACT

A system forms a cardiac conduction block at a location in a heart of a patient without substantially ablating cardiac tissue. The system includes a delivery system coupled to a source of material that is substantially non-ablative with respect to cardiac tissue. The delivery system delivers the material to the location, and the material at the location forms a conduction block without ablating the cardiac cells there. The material may include living cells, such as for example skeletal myocytes, and/or may include a non-living matter such as biopolymers such as a fibrin glue agent, or collagen agents. An expandable member with needle assembly is used to deliver the material so as to form a non-ablative circumferential conduction block at a location where a pulmonary vein extends from an atrium.

16 Claims, 6 Drawing Sheets

U.S. PATENT DOCUMENTS

| | | |
|---|---|---|
| 4,920,980 A | 5/1990 | Jackowski |
| 4,940,064 A | 7/1990 | Desai |
| 4,974,598 A | 12/1990 | John |
| 4,998,933 A | 3/1991 | Eggers et al. |
| 5,007,908 A | 4/1991 | Rydell |
| 5,058,599 A | 10/1991 | Andersen |
| 5,074,313 A | 12/1991 | Dahl et al. |
| 5,103,821 A | 4/1992 | King |
| 5,107,850 A | 4/1992 | Olive |
| 5,130,141 A | 7/1992 | Law et al. |
| 5,158,079 A | 10/1992 | Adams et al. |
| 5,209,229 A | 5/1993 | Gilli |
| 5,222,501 A | 6/1993 | Ideker et al. |
| 5,228,442 A | 7/1993 | Imran |
| 5,231,995 A | 8/1993 | Desai |
| 5,255,679 A | 10/1993 | Imran |
| 5,259,395 A | 11/1993 | Li |
| 5,263,493 A | 11/1993 | Avitall |
| 5,293,868 A | 3/1994 | Nardella |
| 5,293,869 A | 3/1994 | Edwards et al. |
| 5,300,085 A | 4/1994 | Yock |
| 5,311,873 A | 5/1994 | Savard et al. |
| 5,313,943 A | 5/1994 | Houser et al. |
| 5,314,460 A | 5/1994 | Borghi |
| 5,314,461 A | 5/1994 | Borghi |
| 5,324,284 A | 6/1994 | Imran |
| 5,325,860 A | 7/1994 | Seward et al. |
| 5,331,966 A | 7/1994 | Bennett et al. |
| 5,336,222 A | 8/1994 | Durgin, Jr. et al. |
| 5,336,251 A | 8/1994 | Borghi |
| 5,345,936 A | 9/1994 | Pomeranz et al. |
| 5,345,940 A | 9/1994 | Seward et al. |
| 5,366,486 A | 11/1994 | Zipes et al. |
| 5,366,487 A | 11/1994 | Adams et al. |
| 5,366,490 A | 11/1994 | Edwards et al. |
| 5,370,675 A | 12/1994 | Edwards et al. |
| 5,370,678 A | 12/1994 | Edwards et al. |
| 5,385,544 A | 1/1995 | Edwards et al. |
| 5,391,199 A | 2/1995 | Ben-Haim |
| 5,400,796 A | 3/1995 | Wecke |
| 5,403,311 A | 4/1995 | Abele et al. |
| 5,405,376 A | 4/1995 | Mulier et al. |
| 5,409,000 A | 4/1995 | Imran |
| 5,409,453 A | 4/1995 | Lundquist et al. |
| 5,411,524 A | 5/1995 | Rahul |
| 5,421,819 A | 6/1995 | Edwards et al. |
| 5,423,808 A | 6/1995 | Edwards et al. |
| 5,423,811 A | 6/1995 | Imran et al. |
| 5,427,119 A | 6/1995 | Swartz et al. |
| 5,431,649 A | 7/1995 | Mulier et al. |
| 5,433,198 A | 7/1995 | Desai |
| 5,433,708 A | 7/1995 | Nichols et al. |
| 5,435,805 A | 7/1995 | Edwards et al. |
| 5,439,483 A | 8/1995 | Duong-Van |
| 5,450,846 A | 9/1995 | Goldreyer |
| 5,464,431 A | 11/1995 | Adams et al. |
| 5,470,308 A | 11/1995 | Edwards et al. |
| 5,476,503 A | 12/1995 | Yang |
| 5,484,400 A | 1/1996 | Edwards et al. |
| 5,485,849 A | 1/1996 | Panescu et al. |
| 5,487,385 A | 1/1996 | Avitall |
| 5,496,312 A | 3/1996 | Klicek |
| 5,496,360 A | 3/1996 | Hoffmann et al. |
| 5,500,012 A | 3/1996 | Brucker et al. |
| 5,507,802 A | 4/1996 | Imran |
| 5,509,900 A | 4/1996 | Kirkman |
| 5,545,193 A | 8/1996 | Kordis et al. |
| 5,549,641 A | 8/1996 | Ayers et al. |
| 5,549,661 A | 8/1996 | Kordis et al. |
| 5,562,720 A | 10/1996 | Stern et al. |
| 5,564,440 A | 10/1996 | Swartz et al. |
| 5,571,088 A | 11/1996 | Lennox et al. |
| 5,571,159 A | 11/1996 | Alt |
| 5,575,766 A | 11/1996 | Swartz et al. |
| 5,575,772 A | 11/1996 | Lennox |
| 5,575,810 A | 11/1996 | Swanson et al. |
| 5,582,609 A | 12/1996 | Swanson et al. |
| 5,588,432 A | 12/1996 | Crowley |
| 5,605,159 A | 2/1997 | Smith et al. |
| 5,606,974 A | 3/1997 | Castellano et al. |
| 5,607,422 A | 3/1997 | Smeets et al. |
| 5,607,462 A | 3/1997 | Imran |
| 5,609,151 A | 3/1997 | Mulier et al. |
| 5,617,854 A | 4/1997 | Munsif |
| 5,642,736 A | 7/1997 | Avitall |
| 5,645,082 A | 7/1997 | Sung et al. |
| 5,661,133 A | 8/1997 | Leiden et al. |
| 5,674,274 A | 10/1997 | Morgan et al. |
| 5,676,153 A | 10/1997 | Smith et al. |
| 5,676,662 A | 10/1997 | Fleischhacker et al. |
| 5,680,860 A | 10/1997 | Imran |
| 5,681,308 A | 10/1997 | Edwards et al. |
| 5,683,447 A | 11/1997 | Bush et al. |
| 5,687,723 A | 11/1997 | Avitall |
| 5,688,267 A | 11/1997 | Panescu et al. |
| 5,690,611 A | 11/1997 | Swartz et al. |
| 5,693,078 A | 12/1997 | Desai et al. |
| 5,693,622 A | 12/1997 | Wolff et al. |
| 5,697,927 A | 12/1997 | Imran et al. |
| 5,702,433 A | 12/1997 | Taylor et al. |
| 5,716,318 A * | 2/1998 | Manning ................ 600/16 |
| 5,716,389 A | 2/1998 | Walinsky et al. |
| 5,718,241 A | 2/1998 | Ben-Haim et al. |
| 5,720,775 A | 2/1998 | Larnard |
| 5,722,401 A | 3/1998 | Pietroski et al. |
| 5,722,403 A | 3/1998 | McGee et al. |
| 5,722,963 A | 3/1998 | Lurie et al. |
| 5,728,140 A | 3/1998 | Salo et al. |
| 5,730,127 A | 3/1998 | Avitall |
| 5,730,704 A | 3/1998 | Avitall |
| 5,735,280 A | 4/1998 | Sherman et al. |
| 5,735,846 A | 4/1998 | Panescu et al. |
| 5,741,320 A | 4/1998 | Thornton et al. |
| 5,755,663 A | 5/1998 | Larsen et al. |
| 5,755,760 A | 5/1998 | Maguire et al. |
| 5,769,846 A | 6/1998 | Edwards et al. |
| 5,782,239 A | 7/1998 | Webster, Jr. |
| 5,782,898 A | 7/1998 | Dahl et al. |
| RE35,880 E | 8/1998 | Waldman et al. |
| 5,797,842 A | 8/1998 | Pumares et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,413 A | 9/1998 | Swartz et al. |
| 5,800,428 A | 9/1998 | Nelson et al. |
| 5,800,432 A | 9/1998 | Swanson |
| 5,807,249 A | 9/1998 | Qin et al. |
| 5,807,395 A | 9/1998 | Mulier et al. |
| 5,840,031 A | 11/1998 | Crowley |
| 5,840,076 A | 11/1998 | Swanson et al. |
| 5,842,984 A | 12/1998 | Avitall |
| 5,843,154 A | 12/1998 | Osypka |
| 5,885,278 A | 3/1999 | Fleischman |
| 5,921,982 A | 7/1999 | Lesh et al. |
| 5,938,660 A | 8/1999 | Swartz et al. |
| 5,968,981 A * | 10/1999 | Chien et al. ................ 514/557 |
| 5,971,983 A | 10/1999 | Lesh |
| 6,001,093 A | 12/1999 | Swanson et al. |
| 6,012,457 A | 1/2000 | Lesh |
| 6,024,740 A | 2/2000 | Lesh et al. |
| 6,059,726 A | 5/2000 | Lee et al. |

| | | |
|---|---|---|
| 6,063,077 A | 5/2000 | Schaer |
| 6,064,902 A | 5/2000 | Haissaguerre et al. |
| 6,071,279 A | 6/2000 | Whayne et al. |
| 6,071,281 A | 6/2000 | Burnside et al. |
| 6,071,282 A | 6/2000 | Fleischman |
| 6,086,582 A * | 7/2000 | Altman et al. ............ 606/41 |
| 6,090,084 A | 7/2000 | Hassett et al. |
| 6,101,410 A | 8/2000 | Panescu et al. |
| 6,117,101 A | 9/2000 | Diederich et al. |
| 6,128,535 A | 10/2000 | Maarse |
| 6,129,761 A | 10/2000 | Hubbell |
| 6,146,379 A | 11/2000 | Fleischman et al. |
| 6,151,525 A | 11/2000 | Soykan et al. |
| 6,161,543 A | 12/2000 | Cox et al. |
| 6,164,283 A | 12/2000 | Lesh |
| 6,214,002 B1 | 4/2001 | Fleischman et al. |
| 6,238,429 B1 | 5/2001 | Markowitz et al. |
| 6,242,473 B1 | 6/2001 | Hellstrand et al. |
| 6,245,059 B1 | 6/2001 | Clapham |
| 6,261,832 B1 | 7/2001 | Law |
| 6,312,685 B1 | 11/2001 | Fisher et al. |
| 6,443,949 B2 | 9/2002 | Altman |
| 6,453,195 B1 * | 9/2002 | Thompson .................. 607/3 |
| 6,502,576 B1 | 1/2003 | Lesh |
| 6,511,477 B2 | 1/2003 | Altman et al. |
| 6,533,819 B1 | 3/2003 | Urry et al. |
| 6,547,787 B1 | 4/2003 | Altman et al. |
| 6,730,016 B1 * | 5/2004 | Cox et al. .................. 600/37 |
| 2002/0031501 A1 | 3/2002 | Law |
| 2002/0035388 A1 | 3/2002 | Lindemans et al. |
| 2002/0044925 A1 | 4/2002 | Law |
| 2002/0087089 A1 | 7/2002 | Ben-Haim |
| 2002/0123771 A1 | 9/2002 | Ideker et al. |

FOREIGN PATENT DOCUMENTS

| | | |
|---|---|---|
| EP | 0 452 278 A2 | 10/1991 |
| EP | 0 609 182 A1 | 8/1994 |
| EP | 0 672 431 A2 | 9/1995 |
| EP | 0 672 432 A1 | 9/1995 |
| EP | 0 452 278 B1 | 11/1995 |
| WO | WO 90/10471 | 9/1990 |
| WO | WO 93/00958 | 1/1993 |
| WO | WO 93/16632 | 9/1993 |
| WO | WO 93/20767 | 10/1993 |
| WO | WO 93/20886 | 10/1993 |
| WO | WO 94/21165 | 9/1994 |
| WO | WO 94/21167 | 9/1994 |
| WO | WO 94/21168 | 9/1994 |
| WO | WO 95/05781 | 3/1995 |
| WO | WO 95/10318 | 4/1995 |
| WO | WO 95/10319 | 4/1995 |
| WO | WO 95/10321 | 4/1995 |
| WO | WO 95/15115 | 6/1995 |
| WO | WO 96/18303 | 6/1996 |
| WO | WO 96/32885 | 10/1996 |
| WO | WO 96/32897 | 10/1996 |
| WO | WO 97/32525 | 9/1997 |
| WO | WO 97/37607 | 10/1997 |
| WO | WO 97/45156 | 12/1997 |
| WO | WO 98/02150 | 1/1998 |
| WO | WO 98/02201 | 1/1998 |
| WO | WO 98/28039 | 7/1998 |
| WO | WO 98/49957 | 11/1998 |
| WO | WO 99/00064 | 1/1999 |
| WO | WO 00/59395 | 10/2000 |
| WO | WO 01/68814 A2 | 9/2001 |
| WO | WO 02/22206 A1 | 3/2002 |
| WO | WO 02/051495 A2 | 7/2002 |

OTHER PUBLICATIONS

Lesh, MD, Michael D., Interventional Electrophysiology State-of-the-art 1993; American Heart Journal vol. 126, No. 3, Part 1: 686–698; Sep. 1993.

Jais, MD, Pierre et al, A Focal Source of Atrial Fibrillation Treated by Discrete Radiofrequency Ablation; Circulation vol. 95, No. 3, Feb. 4, 1997: 572–576.

Hendricks, MD, Gerhard et al, Catheter Ablation; Current Management of Arrhythmias; Ch IX Nonpharmacologic Management: 373–378; Not date available.

Haissaguerre, MD, Michel et al, Right and Left Atrial Radiofrequency Catheter . . . ; Journal of Cardiovasscular Electrophysiology vol. 7, No. 12, Dec. 1996: 1132–1144.

Fram, Daniel B. et al, Feasibility of Radiofrequency Powered, Thermal Balloon Ablation of Atrioventricular . . . ; PACE, vol. 18, Aug. 1995:1518–1530.

Cox, MD, James L., The Surgical Treatment of Atrial Fibrillation; IV, Surgical Technique; The Journal of Thoracic and Cardiovascular Surgery, Apr., 1991; 101: 584–92.

Cox, MD, James L. et al, The Surgical Treatment of Atrial Fibrillation; I. Summary of the Current . . . ; Journal of Thoracic and Cardiovascular Surgery, Mar. 1991;101: 402–405.

Diederich, Chris J. et al, Induction of Hyperthermia Using an Intracavitary Multielement . . . ; IEEE Transactions on Biomedical Engineering vol. 36, No. 4, Apr. 1989; 432–438.

Diederich, C. J. et al, The Development of Intracavitary Ultrasonic Applicators for Hyperthermia: A Design . . . ; Medical Physics, vol. 17, No. 4, Jul./Aug. 1990.

Avitall, MD, Boaz et al, Physics and Engineering of Transcatheter Cardiac Tissue Ablation; JACC vol. 22, No. 3; Sep. 1993: 921–32.

O'Brien, David P. et al, Flexible Microelectrode Arrays with Integrated Insertion Devices; MEMS '01, 216–219 (2002).

Long, Carlin S. et al, The Cardiac Fibroblast, Another Therepeutic Target For Mending The Broken Heart?; J of Molecular Cell Cardiology, vol. 34, pp. 1273–1278, Mar. 7, 2002.

Suzuki, K. et al, Overexpression of Connexin 43 in Skeletal Myoblasts . . . ; Journal of Thoracic and Cardiovascular Surgery, vol. 122, No. 4, pp. 759–766, Oct. 2001.

Feld, Yair et al, Electrophysiological Modulation of Cardiomyocytic Tissue by Transfected Fibroblasts Expressing . . . ; Circulation, vol. 105, pp. 522–529, Jan. 29, 2002.

Murry, Charles E. et al, Muscle Cell Grafting for the Treatment and Prevention of Heart Failure; J of Cardiac Failure, vol. 8, No. 6, pp. S532–S541, (Suppl. Dec. 2002).

Atkins, B. Zane et al, Myogenic Cell Transplantation Improves In Vivo Regional Performance . . . ; Journal of Heart and Lung Transplant 1999; 18:1173–1180; Dec. 1999.

Janus, Edward D. et al, The Modernization of Asia, Implications for Coronary Heart Disease; Circulation, vol. 94, pp. 2671–2673, Dec. 1, 1996.

Orlic, Donald et al, Bone Marrow Cells Regenerate Infarcted Myocardium; Letters to Nature, vol. 410, pp. 701–705, Apr. 2001.

Reinecke, Hans et al, Transmural Replacement of Myocardium After Skeletal Myoblast Grafting Into . . . ; Cardiovascular Pathology, vol. 9, No. 6,pp. 337–344, Dec. 2000.

* cited by examiner

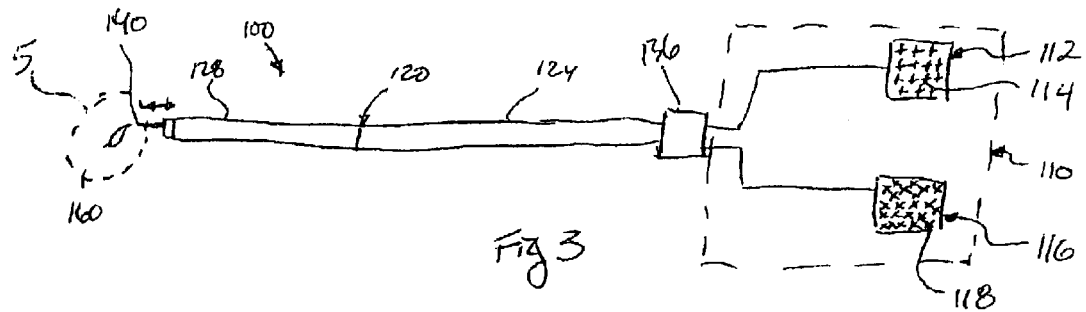
Fig 3
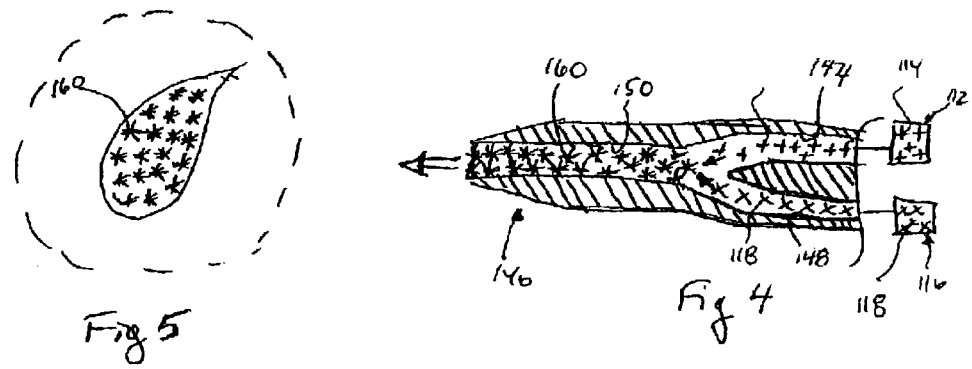
Fig 5
Fig 4
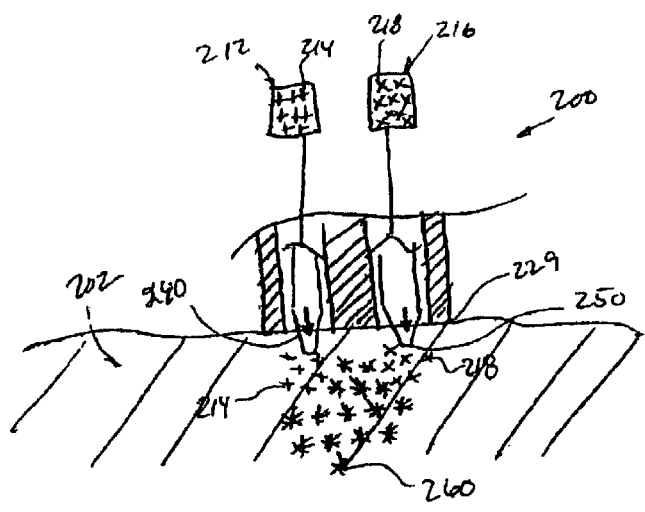
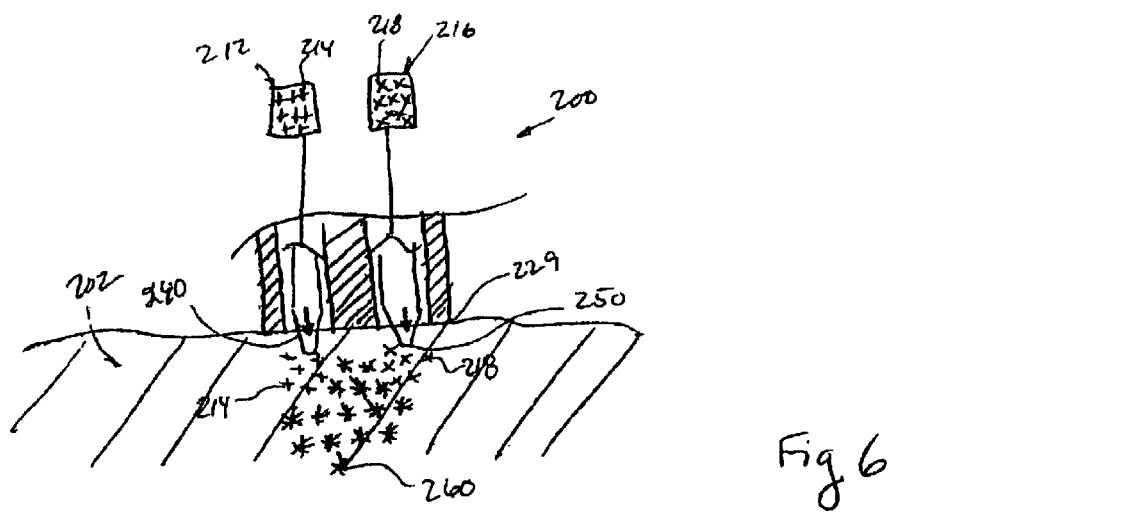
Fig 6

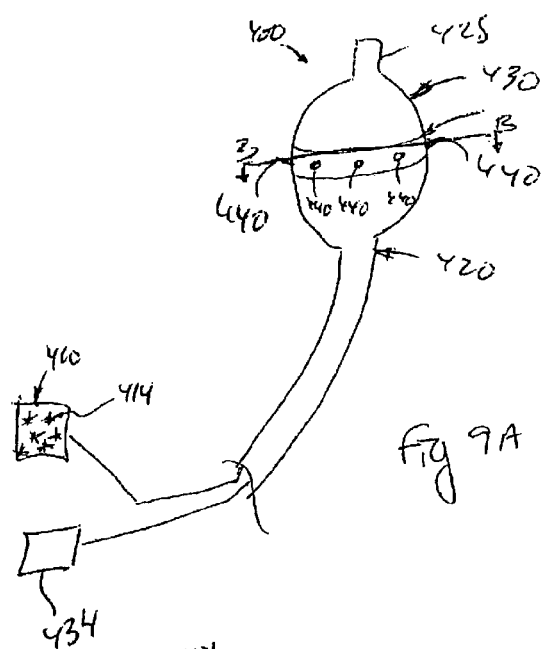
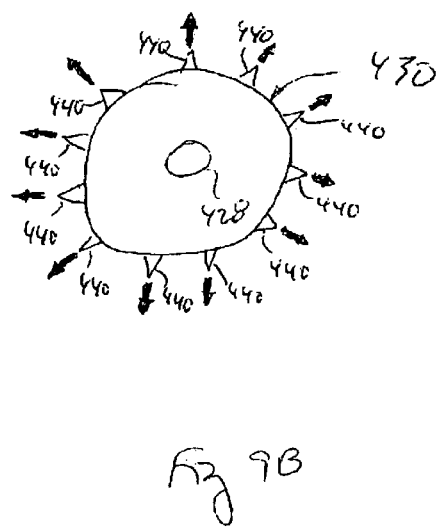
Fig 9A
Fig 9B
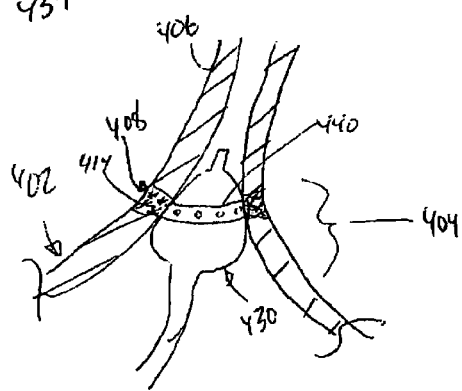
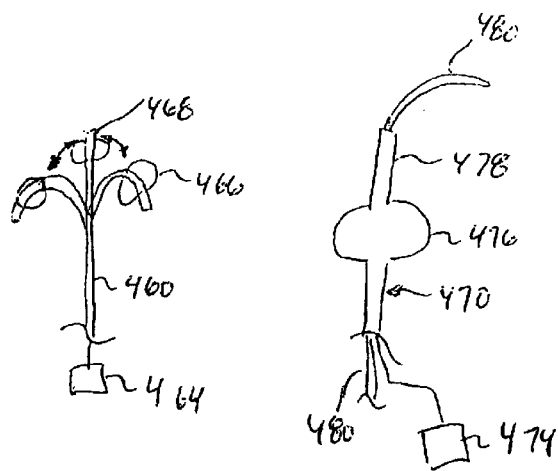
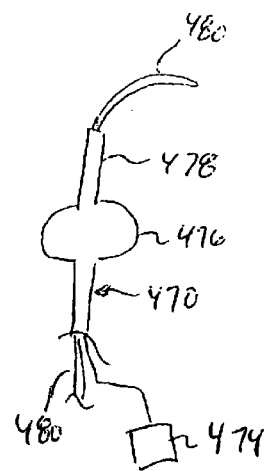
Fig 10
Fig 11
Fig 12

SYSTEM AND METHOD FOR FORMING A NON-ABLATIVE CARDIAC CONDUCTION BLOCK

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention pertains generally to systems and methods for treating medical conditions associated with the heart, and more particularly to surgical devices and procedures for forming conduction blocks at locations associated with the heart that include cardiac tissue.

2. Description of Related Art

Cellular therapy for treating cardiac conditions has been the topic of significant research and development in recent years, generally for the purpose of increasing cardiac conduction or function. In fact, certain types of injected cells have been observed to couple poorly with indigenous cardiac cell tissues, and various prior disclosures have cited a related decrease in conduction transmission as a significant obstacle to the intended cellular therapy. Some disclosures have cited a desire to in fact modify the properties of injected cells to increase the cardiac tissue coupling for enhanced conduction or contractility.

Tissue engineering techniques utilizing skeletal myoblast transplantation for myocardial repair has in particular gained increased attention with the demonstration that skeletal myoblasts survive and form contractile myofibers in normal and injured myocardium. However, the emphasis of myocardial repair has focused on the preservation of myocardial contractility with little attention given to the effects of tissue engineering on cardiac conduction or effects on cardiac arrhythmias.

In addition, according to previous disclosures skeletal muscle cells may be initially injected as myoblast and thereafter differentiate into myotubes/myofibers. The conduction properties of myoblasts and myotubes are significantly different. Additionally, depending on how old the myoblasts are, they can vary in conduction properties. Therefore, following the injection of certain preparations of myoblasts, a heterogeneous mileau of cells may result which can produce unpredictable insulation results. However, the use of myoblast injections for creation of conduction blocks to treat arrhythmias should nevertheless be effective.

Cardiac arrhythmias are abnormal conditions associated with the various chambers and other structures of the heart, and are typically treated by drug therapy, ablation, defibrillation or pacing. Ablation is generally a treatment technique intended to create conduction blocks to intervene and stop aberrant conduction pathways that otherwise disturb the normal cardiac cycle. Typical ablation technology for forming conduction blocks uses systems and methods designed to kill tissue along the pathway, such as by applying energy to destroy cells via hyperthermia such as with electrical current (e.g. radiofrequency or "RF" current), ultrasound, microwave, or laser energy, or via hypothermia using cryotherapy, or chemical ablation such as destructive ethanol delivery to tissue. Despite the significant benefits and successful treatments that have been observed by creating conduction blocks using various of these techniques, each is associated with certain adverse consequences. For example, ablative hyperthermia or other modes causing necrosis have been observed to result in scarring, thrombosis, collagen shrinkage, and undesired structural damage to deeper tissues.

There is a need for improved systems and methods for treating cardiac arrhythmias.

There is in particular a need for improved systems and methods for forming conduction blocks at locations along cardiac tissue structures without substantially ablating cardiac tissue.

BRIEF SUMMARY OF THE INVENTION

It is an object of the invention to treat cardiac arrhythmias by forming conduction blocks without substantially ablating cardiac tissue.

It is also an object of the invention to treat cardiac arrhythmias by forming a conduction block without requiring hyperthermia or hypothermia treatment of cardiac tissue.

It is also an object of the invention to treat cardiac arrhythmias without requiring direct surgery techniques.

It is a further object of the invention to treat cardiac arrhythmias using less invasive or minimally invasive systems and methods.

Accordingly, one aspect of the invention is a system for treating a cardiac arrhythmia in a heart of a patient that includes a delivery system coupled to a source of material that is substantially non-ablative with respect to cardiac cells. The delivery system is adapted to deliver a volume of the material from the source to a location associated with the patient's heart that includes cardiac cells such that the material is adapted to form a substantially non-ablative conduction block at the location.

In one mode of this aspect, the material is a living material, which in a highly beneficial embodiment is living cells. According to a further beneficial variation of such embodiment, the living cells are myocytes, such as skeletal myocytes.

In another mode, the material is a non-living material, which in a highly beneficial embodiment is a polymer agent, and in another variation is collagen or a precursor or analog or derivative thereof.

According to a further beneficial variation of the polymer embodiment, the polymer agent forms a fibrin glue. In an additional feature with respect to this variation, the source of material may therefore include a first source of a first precursor material and a second source of a second precursor material. The delivery system is adapted to couple to the first and second sources of first and second precursor materials, respectively, and the first and second precursor materials are adapted to be mixed to form fibrin glue that forms the conduction block at the location. In still a further feature, the delivery system may be in particular adapted to mix the first and second precursor materials prior to delivery to the location. Alternatively, the delivery system can be adapted to deliver the first and second precursor materials to the location separately such that they are mixed at the location.

According to another mode, the material of the source is adapted to be delivered by the delivery system into an extracellular matrix between cardiac cells at the location. In one embodiment of this mode, the material is adapted to intervene with gap-junctions between cardiac cells at the location.

According to still a further mode, the delivery system is adapted to deliver the material to the location along a ventricle wall of a ventricle in the patient's heart.

In another mode, the delivery system is adapted to deliver the material to the location along an atrial wall of an atrium in the patient's heart.

In still another mode, the delivery system is adapted to deliver the material to the location where a pulmonary vein extends from an atrium in the patient's heart, such as at the pulmonary vein ostium, or at locations where cardiac tissue extends into pulmonary veins along the pulmonary vein wall or immediately surrounding the pulmonary vein along the posterior atrial wall.

In one further embodiment of this mode, the delivery system is adapted to deliver the material along a circumferential region of tissue at the location.

According to one variation of this embodiment, the delivery system includes an expandable member that is adapted to engage the circumferential region of tissue. Such expandable member in according to one beneficial feature may be an inflatable balloon. In a further feature, the delivery system is adapted to deliver the material to the circumferential region of tissue when the circumferential region of tissue is engaged by the inflatable balloon. According to another feature of this expandable member variation, the delivery system further includes at least one needle cooperating with the expandable member. The delivery system according to this feature is configured to fluidly couple the at least one needle to the source of material and to deliver the material to the location via the needle.

According to still a further mode of this aspect, the material of the source includes living cells in combination with a second material that is non-living and that is adapted to enhance formation of the conduction block. In one highly beneficial embodiment of this mode, the second material is a polymer agent, which in one beneficial variation forms a fibrin glue that is adapted to form the conduction block. In another embodiment, the second material is collagen or a precursor or analog or derivative thereof.

In another embodiment of this mode, the second material is adapted to enhance retention of the living cells at the location. In still another embodiment, the second material is adapted to intervene at gap-junctions between adjacent cells at the location.

Another aspect of the invention is a system for treating a cardiac arrhythmia in a heart of a patient that includes a delivery system that cooperates with means for forming a conduction block at a location associated with the patient's heart that includes cardiac cells and such that cardiac cells are not substantially ablated.

In one mode of this aspect, the means for forming the conduction block includes a source of material that is substantially non-ablative with respect to cardiac cells and that is adapted to form a conduction block when delivered to the location. According to this mode, the delivery system is adapted to couple to the source of material and to deliver a volume of the material from the source to the location that is substantially non-ablative with respect to cardiac cells and that forms the conduction block.

In one embodiment of this mode, the material of the source that is adapted to form the substantially non-ablative conduction block is a living material, which in one highly beneficial variation includes cells, which cells in a further feature may be myoblasts such as skeletal myoblasts.

In another embodiment of this mode, the material of the source that is adapted to form the substantially non-ablative conduction block is non-living material, which in one highly beneficial variation is a polymer agent, and which polymer agent in a further beneficial feature may be a fibrin glue agent, such as the type formed by first and second precursor materials. Further to this latter feature, the source of material may therefore include first and second substantially isolated sources of first and second precursor materials, respectively, that are adapted to be mixed to form fibrin glue which forms the conduction block at the location. In another variation, the material is collagen or precursor or analog or derivative thereof.

According to another mode, the means for forming a conduction block includes means for forming a substantially circumferential conduction block along a circumferential region of tissue at a location where a pulmonary vein extends from an atrium. In one embodiment of this mode, the means for forming the substantially circumferential conduction block includes means for delivering a material to the circumferential region of tissue that is substantially non-ablative with respect to cardiac cells but that forms the conduction block.

According to yet another mode, the delivery system includes means for locating the location as a region associated with the cardiac arrhythmia. This means for locating the location according to one embodiment of this mode includes an electrode that is adapted to couple to a monitoring system for mapping electrical conduction in the heart.

According to still a further mode, the means for forming the conduction block comprises means for physically separating cardiac cells at the location.

Another aspect of the invention is a method for treating a cardiac arrhythmia in a heart of a patient by forming a conduction block at a location associated with the patient's heart that includes cardiac cells. Further to this method, the conduction block is formed by delivering a material to the location and without substantially ablating cardiac cells.

According to one mode of this aspect, the conduction block is formed by delivering a non-living material to the location that is substantially non-ablative with respect to cardiac cells. In one embodiment of this mode, the material forms the conduction block by intervening with gap-junctions of cardiac tissue with the material.

In another embodiment of this mode, the conduction block is formed by delivering a polymer to the location, which polymer agent may be for example a fibrin glue agent. According to one variation of this mode, the polymer delivery further includes mixing first and second precursor materials within the body of the patient to form the polymer in vivo.

In another embodiment of this mode, the conduction block is formed by delivering a collagen material to the location, or precursor or analog or derivative thereof.

According to another mode of this method, the conduction block is formed by delivering a living material to the location, such as in a highly beneficial embodiment living cells. In a further variation, the living cells being delivered are myocytes.

According to yet another mode of this method, the region to which the material is being delivered is located along a ventricular wall of a ventricle of the patient's heart.

In another mode, the region to which the material is being delivered is located along an atrial wall of an atrium of the patient's heart.

Another aspect of the invention is a method for treating a cardiac arrhythmia in a heart of a patient by forming a conduction block at a location associated with the patient's heart that includes cardiac cells by delivering living cells to the location. In one highly beneficial mode of this aspect, the conduction block is formed by delivering myoblasts to the location. In another beneficial mode the conduction block is formed by delivering fibroblasts to the location. In another mode the conduction block is formed by delivering stem cells to the location. In another mode, the conduction block is formed by delivering living cells and a second material that is adapted to enhance formation of the conduction block than if the cells were delivered without the second material. In one embodiment, the second material enhances retention of the living cells at the location. In another embodiment, the second material intervenes at gap junctions between cells. In another embodiment, the second material provides for a physical separation between cells at the location. In another embodiment the second material is a polymer agent, which in a beneficial variation is a fibrin glue or precursor or analog or derivative thereof. In another embodiment the second material is collagen or precursor or analog or derivative thereof.

Another aspect of the invention is a system for treating a cardiac arrhythmia in a heart of a patient that includes a delivery system that is coupled to an injectable polymer agent. The delivery system is adapted to deliver the injectable polymer agent to a location associated with the patient's heart that includes cardiac cells.

In one mode, the delivery system coupled to the injectable polymer is not coupled to a source of living cells.

In another mode of this aspect, the delivery system is adapted to provide intracardiac delivery of the injectable polymer agent to the location via at least one of the cardiac chambers.

In another mode, the injectable polymer agent is a fibrin glue agent.

In another mode, the injectable polymer agent includes first and second precursor materials that are adapted to be mixed to form a polymer. Further to this mode, in one embodiment the delivery system is adapted to mix the first and second precursor materials before delivering a polymer formed thereby to the location. In another embodiment, the delivery system is adapted to deliver the first and second precursor materials to the location separately such that they mix and form the polymer at the location.

In another mode of this aspect, the delivery system includes at least one needle that is used to deliver the injectable polymer agent.

In another mode, the delivery system includes a catheter having an elongate body with a proximal and distal end portions and at least one lumen extending between a proximal port located along the proximal end portion and a distal port located along the distal end portion. The proximal port is adapted to couple to a source that contains at least a part of the injectable polymer agent.

Further to this mode, in one embodiment the catheter further includes at least one electrode located along the distal end portion. The electrode is adapted to be coupled to a monitoring system to monitor electrical signals in the heart via the electrode so as to identify the location for delivery of the injectable polymer agent to thereby form the conduction block.

Another aspect of the invention is a system for treating a cardiac arrhythmia in a heart of a patient that includes a delivery system that is coupled to a source of injectable material that includes collagen or a precursor or analog or derivative thereof. The delivery system is adapted to deliver the injectable material to a location associated with the patient's heart that includes cardiac cells.

Another aspect of the invention is a method for treating a medical condition associated with a heart of a patient by delivering a polymer agent into a region of cardiac tissue within the heart of the patient.

In one mode of this aspect, the method includes delivering the polymer agent into the region of cardiac tissue without delivering living material such as cells into the region. In another mode, the polymer agent being delivered into the region is a fibrin glue agent. According to one embodiment of this mode, the delivery of the fibrin glue agent includes forming the fibrin glue in-vivo by mixing a first precursor material and a second precursor material within the patient's body.

Another aspect of the invention is a method for treating a medical condition associated with a heart of a patient by delivering a material that includes collagen or a precursor or analog or derivative thereof into a region of cardiac tissue within the heart of the patient.

Further aspects, modes, embodiments, variations, and features of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only:

FIG. 4 is an exploded view of a distal tip portion of a needle according to one further embodiment for use according to a system of the invention such as that shown in FIG. 3.

FIG. 5 shows an exploded view of a drop of material agent delivered through a needle according to the invention as shown in region 5 in FIG. 3.

FIGS. 13A–B show schematic view of two representative cardiac cells during two modes according to the invention, wherein FIG. 13B shows the cells physically separated by injection of a material into the junction between the cells according to one embodiment of the invention.

DETAILED DESCRIPTION OF THE INVENTION

Referring more specifically to the drawings, for illustrative purposes the present invention is embodied in the apparatus generally shown in FIG. 1 through FIG. 13B. It will be appreciated that the apparatus may vary as to configuration and as to details of the parts, and that the method may vary as to the specific steps and sequence, without departing from the basic concepts as disclosed herein.

This invention relates generally to the prior patent applications previously filed and co-pending herewith: U.S. provisional application Ser. No. 60/431,287 filed on Dec. 6, 2002; and U.S. non-provisional application Ser. No. 10/329,295, which are herein incorporated in their entirety by reference thereto.

Figure 1:
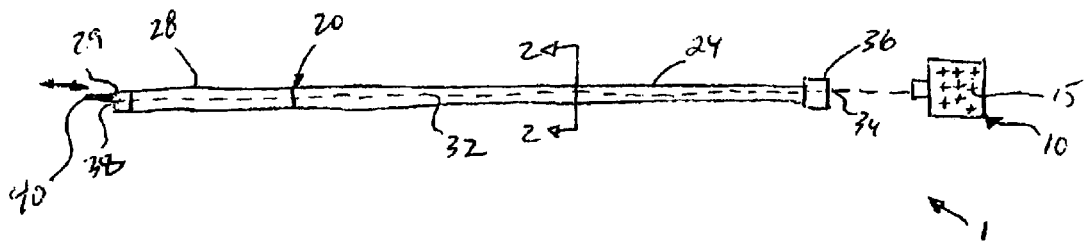
FIG. 1 is a schematic view of various components of a system for creating cardiac conduction blocks according to one embodiment of the invention.

FIG. 1 shows one embodiment of the invention that provides a cardiac treatment system 1 that includes a source of material 10 and a delivery catheter 20. Delivery catheter 20 is adapted to couple to source of material 10 and to deliver material 15 to a region of a heart in a patient, as shown for example in FIG. 2. More specifically, according to this embodiment, delivery catheter 20 has an elongate body 22 with a proximal end portion 24, a distal end portion 28, and a lumen 32 extending therethrough between proximal and distal ports 34,38 located along proximal and distal end portions 24,26, respectively. Proximal port 34 includes a proximal coupler 36 that is adapted to couple to a coupler (not shown) on source of material 10.

Delivery catheter 20 includes a needle 40 that is adapted to extend beyond distal tip 29 of catheter 20 and into tissue and further to deliver material 15 from source 10 into such tissue. Needle 40 may be fixed relative to catheter 20, or in a beneficial variation is moveable, such as axially, as shown in FIG. 1 by axial reference arrow.

The assembly of delivery catheter 20 and needle 40, in a highly simplified form, may include simply a single lumen shaft for catheter body 20 having a single lumen 32 which slideably houses needle 40 that further includes its own delivery lumen 46 for delivering material 15 as an agent into the target tissue. This arrangement is shown for example in cross-section in FIG. 2A. Alternatively, a multi-lumen design may be incorporated, as shown in variations in FIGS. 2B–C as follows.

Figure 2A:
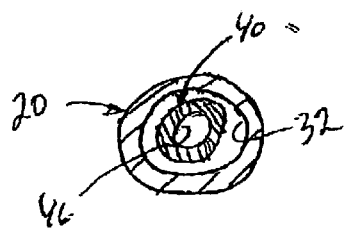
FIG. 2A is a transverse cross-sectional view of one catheter embodiment such as taken along line 2—2 through the catheter shown in the system of FIG. 1.
Figure 2B:
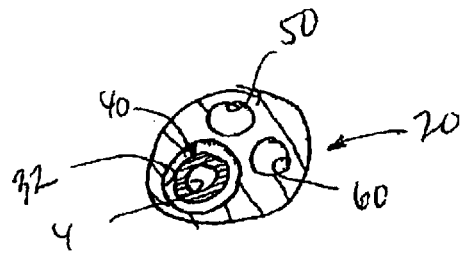
FIG. 2B is a transverse cross-sectional view according to another catheter embodiment in a similar view to that shown in FIG. 2A.

FIG. 2B shows a cross section of a multi-lumen design with needle 40 residing within catheter lumen 32, and also further providing additional lumens 50 and 60 in catheter 20. These additional lumens may have various different functions, depending upon the particular needs.

Figure 2C:
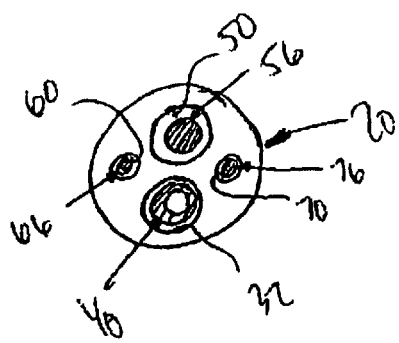
FIG. 2C is a transverse cross-sectional view according to still another catheter embodiment in a similar view to that shown in FIG. 2A.

In the particular variation shown in FIG. 2C, lumen 50 houses a pull-wire 56, whereas lumens 60 and 70 house lead wires 66 and 76. Pull-wire 56 extends between a first securement point at tip 29 and an actuator (not shown) along proximal end portion 24 that is adapted to allow for axial manipulation of pull-wire externally of the body, to thereby deflect distal end portion 28 in-vivo. For deflectable tip designs, certain other material properties are generally taken into account, such as catheter shaft design, flexibility of material chosen for shaft construction, etc., and various other substitute deflection or other manipulation designs or techniques are also contemplated. For example, rather than pull-wire, push wires may be used, or other members than wires such as polymer filaments or fibers, or torsional members. In another alternative design not shown, a guidewire tracking member is provided to work over a guidewire as a rail for remote positioning in-vivo.

Lead wires 66 and 76 extend between a mapping electrode, such as may be provided at tip 29 or otherwise along distal end portion 28, and a proximal electrical coupler that is adapted to couple to a mapping monitoring assembly to provide an overall mapping system with catheter 20 for determining the location for material injection to form a conduction block. General mapping electrode configurations, or combinations of such electrodes, may be suitable for such use according to one of ordinary skill. Moreover, the mapping electrode may be radiopaque for x-ray visualization. To this end, other radiopaque tip markers may also be deployed for such visualization, or other markers or visualization techniques may be used according to one of ordinary skill, such as ultrasound (for example either intravascular, intracardiac, or transesophageal), magnetic resonance imaging ("MRI"), or other suitable modes.

It is also contemplated that needle 40 may take many different forms, such as a relatively straight sharp-tip needle, or may be a hollow screw-shaped needle or other mechanism, such as to aid in anchoring at the desired location.

Moreover, catheter 10 may be adapted to provide delivery of needle 40 at other places than at tip 29, such as along the side wall of the elongate body of distal end portion 28 of catheter. In addition, multiple needles may be deployed such as along a length of catheter 20 in order to form conduction blocks along a prescribed length. To that end, the same needle may be used at different locations, such as delivery through different lumens to different ports along catheter 20, or multiple needles deployed simultaneously or sequentially.

Source of material 10 includes an injectable material 15 that is adapted to form a conduction block in cardiac tissue structures without substantially ablating the cardiac tissue. Examples of highly beneficial materials for use according to the invention include: cells, polymers, or other fluids or preparations that interfere with intercellular junctions, such as impeding communication across or physically separating cellular gap junctions. Another highly beneficial example includes an injectable material containing collagen, or a precursor or analog or derivative thereof.

More specific modes of the invention using cells include myoblasts, fibroblasts, stem cells, or other suitable cells that provide sufficient gap junctions with cardiac cells to form the desired conduction block. With further respect to cell delivery, they may be cultured from the patient's own cells, or may be foreign to the body, such as from a regulated cell culture.

Tissue engineering techniques utilizing skeletal myoblast transplantation for myocardial repair has gained increased attention with the demonstration that skeletal myoblasts survive and form contractile myofibers in normal and injured myocardium. However, the emphasis of myocardial repair has focused on the preservation of myocardial contractility with little attention given to the effects of tissue engineering on cardiac conduction or arrhythmogenesis.

According to embodiments of the present invention using "myoblasts" as a chosen living cell material to be delivered to effect a conduction block, However, notwithstanding such prior observations, use of myoblasts according to certain embodiments of the present invention adapts delivery of these cells in a highly localized manner in order to focus the conduction blocking effects in a positive manner to in fact provide the opposite results versus previous observations—cure arrhythmias with localized, cellular conduction blocks.

Fibroblasts are another alternative cell of the type considered highly beneficial mode for creating conduction blocks via cell therapy. In one particular beneficial regard, fibroblasts do not undergo a transition stage from proliferating to mature cells such as skeletal myoblasts. Fibroblasts therefore have a more homogeneous excitation pattern as compared to skeletal muscle. Fibroblasts' electrophysiological properties are fairly consistent from one fibroblast to the next, and are believed to be effective for blocking conduction. Therefore, in one illustrative embodiment using fibroblasts to block VT for example, very similar responses can be predicted between batches/injections.

Cell therapy for treating cardiac arrhythmias according to various of the present embodiments is considered one mode (though highly beneficial) of a still broader aspect of the invention which provides a non-ablative means for creating conduction blocks in cardiac tissue structures, more specifically associated with the cardiac chambers. This aspect provides immense benefit in providing the intended therapy without many of the other side effects and shortcomings of other conventional techniques for forming cardiac conduction blocks, such as in particular using cardiac ablation.

For example, hyperthermia and thus collagen shrinkage and other substantial scarring responses to other conventional ablation energy delivery modalities is substantially avoided. This has particular benefit for example in preventing occlusion, such as in forming conduction blocks in or around a location where a pulmonary vein extends from an atrium in order to treat or prevent atrial fibrillation.

In addition, cell therapy is generally accomplished in a highly localized manner, whereas many ablation techniques suffer from control of energy delivery and extent of impact therefrom in tissues at or beyond the targeted location. For example, charring associated with the high temperature gradient necessary to form transmural conduction blocks using many RF energy ablation devices techniques is avoided. In another regard, undesired energy dissipation into surrounding tissues is often observed using many conventional ablation techniques and is also avoided using the substantially non-ablative cellular therapy systems and methods of the present invention.

Accordingly, the present invention contemplates a broad scope with respect to providing conduction blocks to treat cardiac arrhythmias without substantially ablating cardiac tissue. As such, other suitable modes than cellular therapy are contemplated according to this aspect of the invention.

For example, a further highly beneficial embodiment of the invention provides a system and method for delivering a non-ablative, non-living media into a region of cardiac tissue for the purpose of forming a cardiac conduction block there. More specifically, certain biopolymer agents such as fibrin glue agent may be highly beneficial agents for such delivery and use. In another example, collagen, or precursor or analog or derivative materials thereof, is further considered a highly beneficial agent for this purpose, in particular in injectable form, which may further include for example a carrier or matrix that adapts the collagen for delivery and may or may not be otherwise be retained with the collagen when implanted to the location, or may otherwise be transported or metabolized, etc., at the injection site.

Embodiments of material 15 may include primarily or only one material such as according to the examples above, or may include combinations of materials. For example, embodiments of material 15 that includes cells may include other materials, such as fluids or other substrates to provide the cells in an overall preparation as a cellular media that is adapted to be injected, such as in particular through delivery lumen 32 of delivery catheter 10. In one particular example that has been observed to be useful, material 15 may include skeletal myoblasts or other suitable substitute cells in combination with a biopolymer agent such as fibrin glue agent, which may itself be provided as two precursor materials that are mixed to form fibrin glue that assists in forming the conduction block when delivered with cells at the desired location within the heart. Collagen or preparations thereof, including precursors or analogs or derivatives of collagen, is also considered useful in such combination.

According to still a further embodiment of the invention, a preparation of living material, such as for example cells, in combination with a non-living material is delivered into cardiac tissue structures to form a conduction block there. In one further more detailed embodiment, the non-living material is adapted to enhance retention of the cells being delivered into the location where the conduction block is to be formed. In another regard, the non-living material is adapted to further contribute to forming the conduction block, such as by intervening to the gap-junctions between cells in the injected region. One particular example of a material that provides significant benefit in such combination with cellular therapy is fibrin glue. More specifically, fibrin glue has been observed to provide enhanced retention of cells such as myoblasts that are injected into cardiac tissue in order to treat damaged cardiac structures, such as infarct regions of a heart, as further developed by reference to one of the Examples below.

Notwithstanding the significant benefit of using fibrin glue in combination with cell delivery for treating cardiac arrhythmias, other suitable substitute materials having similarly beneficial effects in such combination are also contemplated, such as other polymers or molecular scaffolds or materials that intervene sufficiently to inter-cellular gap junctions or otherwise impact the extracellular matrix in cardiac tissue structures to substantially block arrhythmic conduction from propagating. Moreover, collagen or precursors or analogs or derivatives thereof are further considered useful for this purpose, either in addition or in the alternative to fibrin glue.

Figure 3:
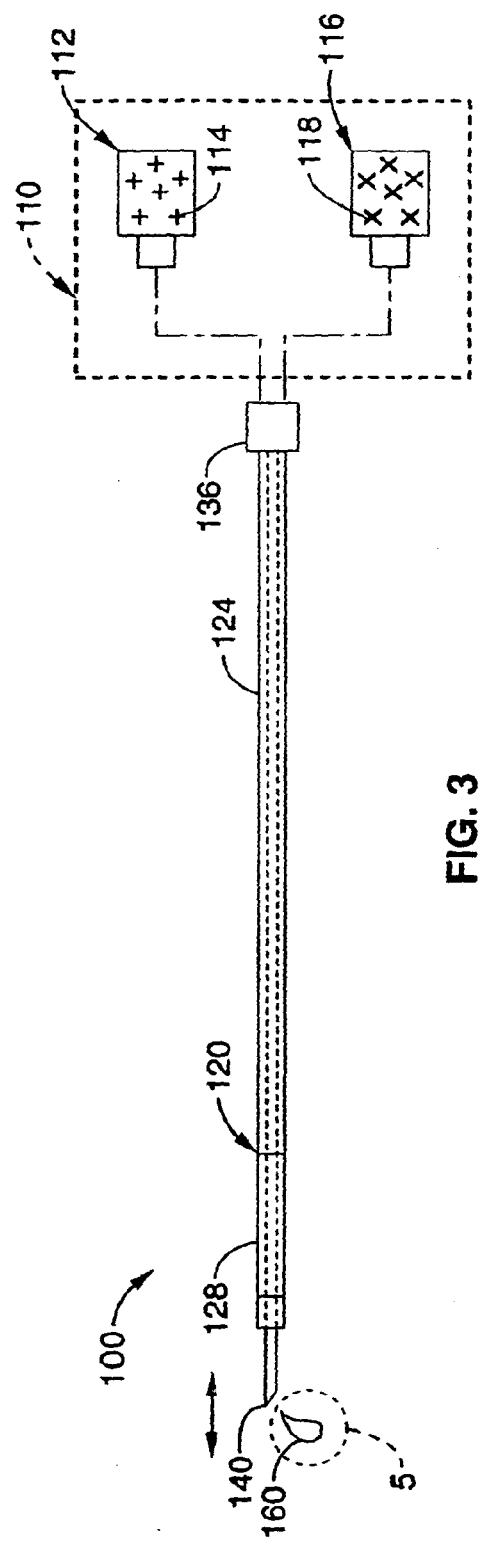
FIG. 3 is a schematic view of various components of another system for creating cardiac conduction blocks according to another embodiment of the invention.

For further illustration, FIG. 3 shows a further embodiment of the invention that provides a delivery catheter 120 that is adapted to couple to two sources 112,116 of two separate materials 114,118, respectively. In this regard, such combination is considered where reference to a "source of material" is elsewhere herein described, and is thus illustrated as a combination source of material 110 in FIG. 3. In this particular embodiment, the two materials 114,118 are two precursor materials to forming fibrin glue, and their combined delivery, either as the separate precursor materials that are later mixed, or in combined form mixed as fibrin glue, is hence considered a fibrin glue "agent". Thus, "agent" in this use is intended to mean the end result, or the necessary combination of precursor material components that lead to the resultant material.

Accordingly, a system 100 as shown in FIG. 3 and by further reference to FIGS. 4 and 5, is adapted to deliver precursor materials 114,118 into the body separately, where they are therein mixed and delivered through needle 140 beyond tip 129 into tissue as a mixed form of fibrin glue 160. An exemplary needle assembly 140 shown in FIG. 5 for accomplishing this objective delivers precursor materials 114,118 via separate lumens 144,148, respectively, that converge into mixing lumen 150 related to needle assembly 140 wherein fibrin glue 160 is formed just prior to injection via needle 140 as an injected fibrin glue, as shown in exploded view in FIG. 5.

It is contemplated that the assembly and various components of system 100 shown by way of the embodiments in FIGS. 3–5 are illustrative, and other suitable substitutes may be used in order to achieve the objective of delivering two precursor materials and mixing them to form the media for injection. For example, in certain circumstances, they may be mixed prior to delivery into the distal portions of catheter 120, such as at a mixing chamber in proximal coupler 136, or prior to coupling to delivery catheter 120. To this end, one coupler may be used to couple to each of multiple sources of material for delivery, or multiple proximal couplers may be used.

Figure 6:
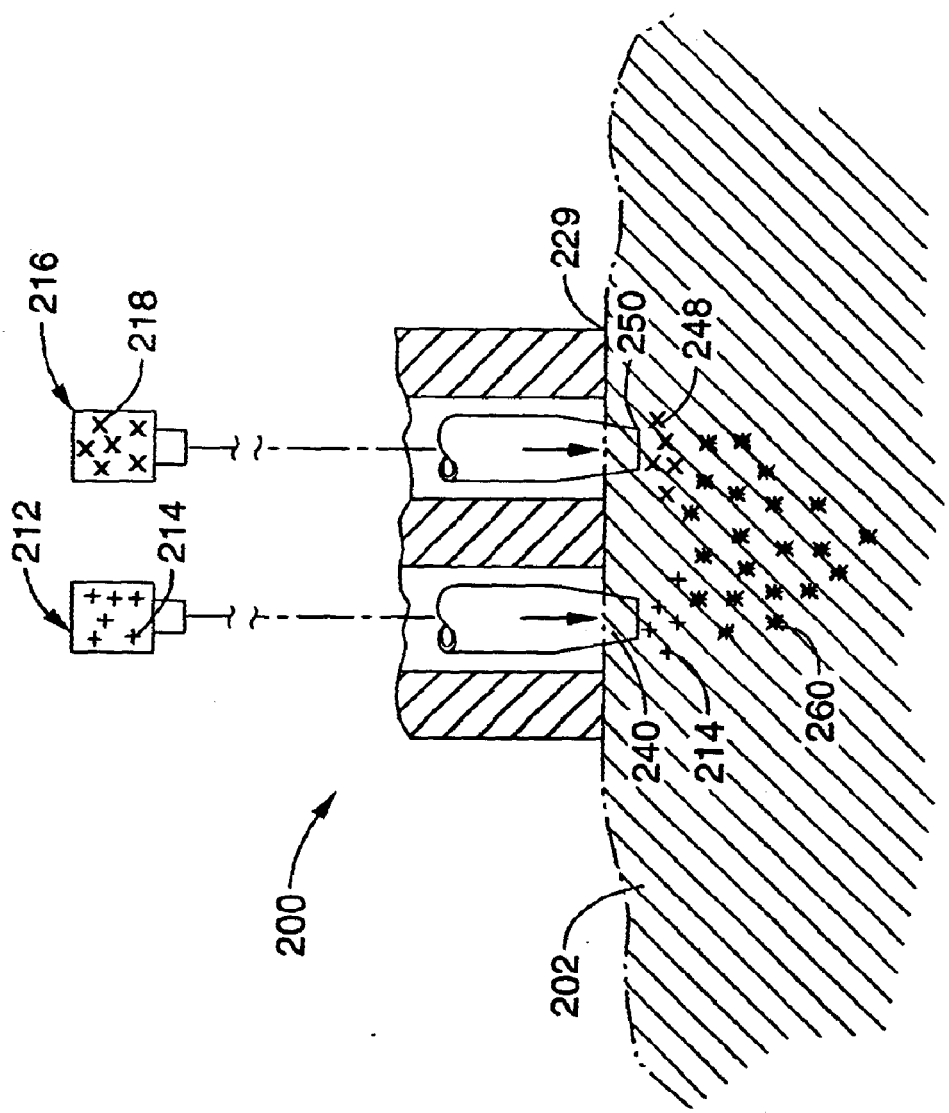
FIG. 6 shows a partially cross-sectioned view of a distal tip portion of another non-ablative material delivery system for forming a cardiac conduction block according to another embodiment of the invention.
Figure 7A:
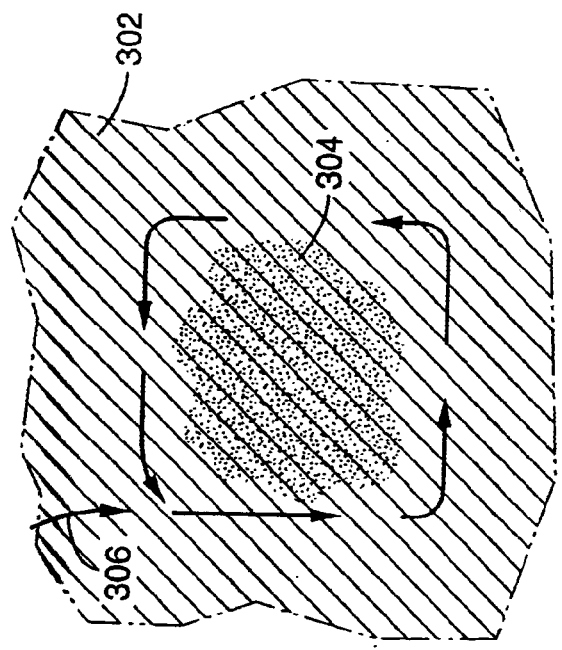
Figure 7B:
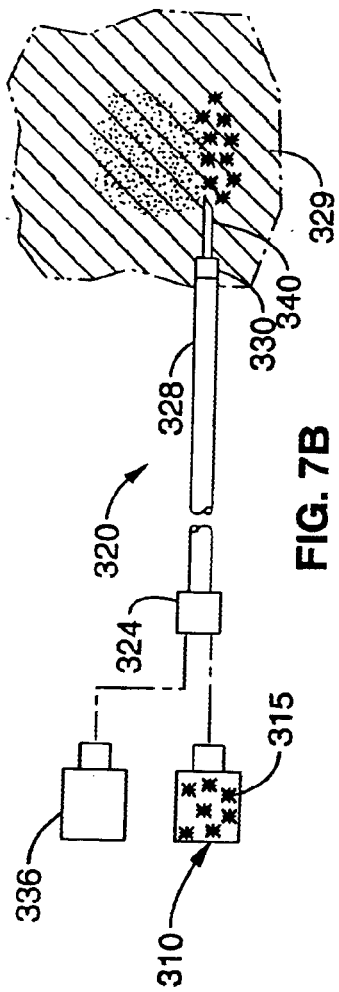
Figure 7C:
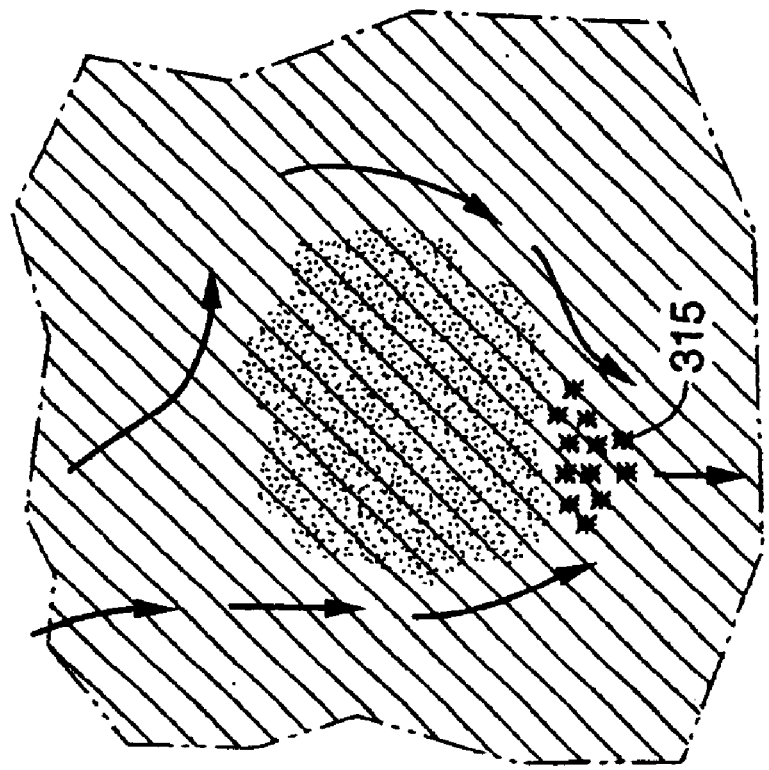
Figure 8:
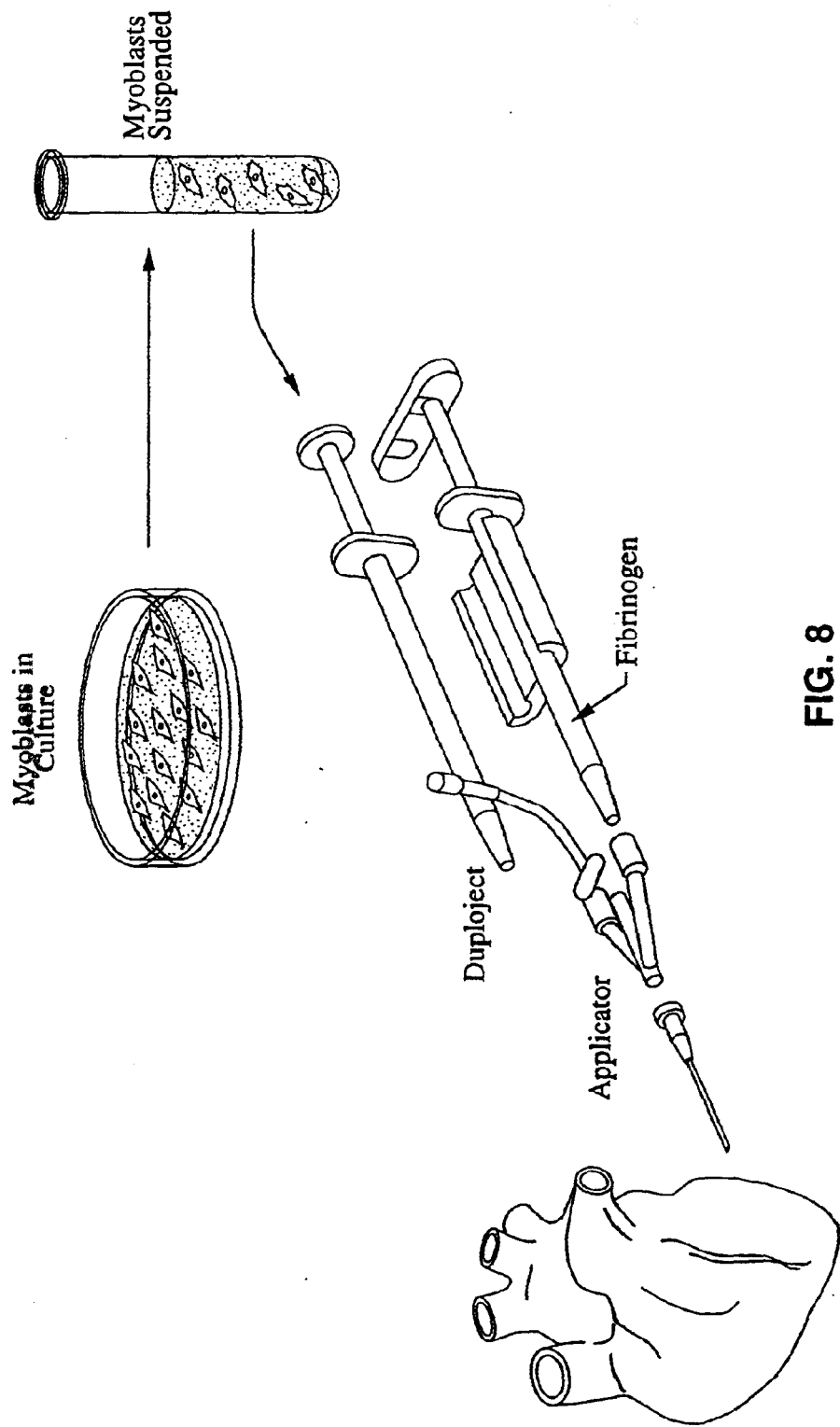

Still further, more than one delivery device may be used for each of two materials being delivered. For example, FIG. 6 shows a schematic view of a system 200 wherein a distal end 229 of catheter 220 in contact with a reference region of cardiac tissue 202. In this embodiment, two separate and distinct needles 240,250 are used to deliver each of two materials 214,218, respectively, from sources 212,216, also respectively, located outside of the patient's body. In this manner, two precursor materials are delivered separately into the tissue 202 where they mix to form fibrin glue 260 within the tissue structure. This provides the benefit of preventing unwanted clogging of the respective delivery lumen within catheter 220 during delivery to the remote in-vivo tissue location. Further to this example, various other structures are assumed to form a part of the overall system 200, such as for catheter 220, including for example an actuator (not shown) that may be one common actuator or multiple independent actuators for advancing needles 240,250 into tissue 202, and/or otherwise injecting the materials 214,218 respectively therethrough.

In addition, the systems 100 and 200 just described are illustrated for use with fibrin glue agents that include a combination of two precursor materials. However, other materials may be substituted for use in such systems, and such systems may be appropriately modified for a particular material delivery. For example, cells may be delivered in combination with a second material according to either system 100 or 200. In addition, such second material may itself be a fibrin glue or other biopolymer agent, which may illustrate further multiples of sources and delivery lumens.

For further understanding, the embodiment of FIGS. 3–4 may be combined with that of FIG. 6 as follows. A source such as source 212 in FIG. 6 may include cells as material 214 to be delivered. However, source 216 in that embodiment may itself include two separate sources that are precursor fibrin glue agent materials, and thus needle 250 of the FIG. 6 embodiment may be of the type shown for needle 140 in FIG. 4.

Figure 7A:
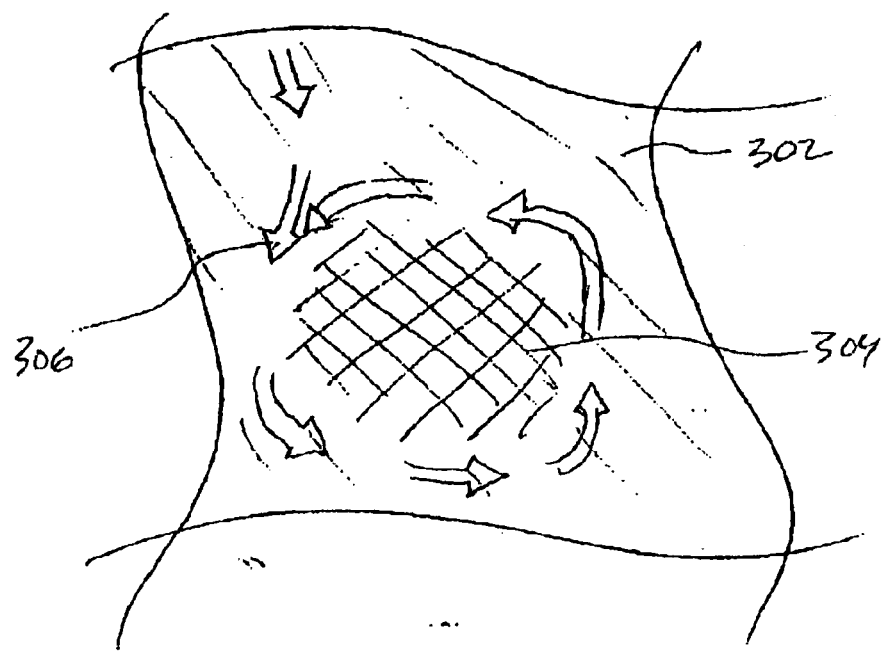
FIGS. 7A–C show exploded views of an infarct region of a cardiac chamber during sequential modes of using the present invention, respectively.
Figure 7B:
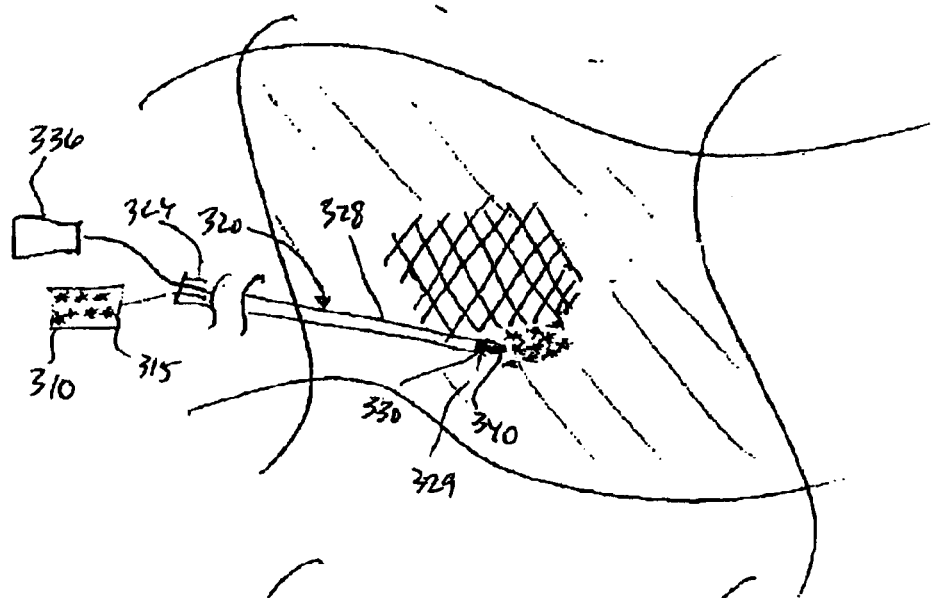
Figure 7C:
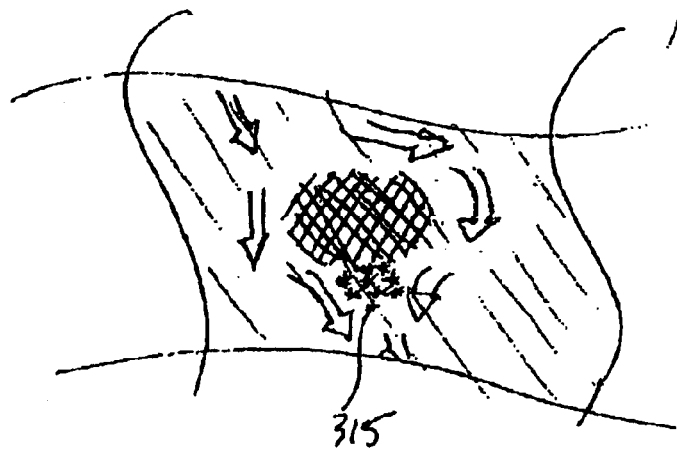
Figure 8:
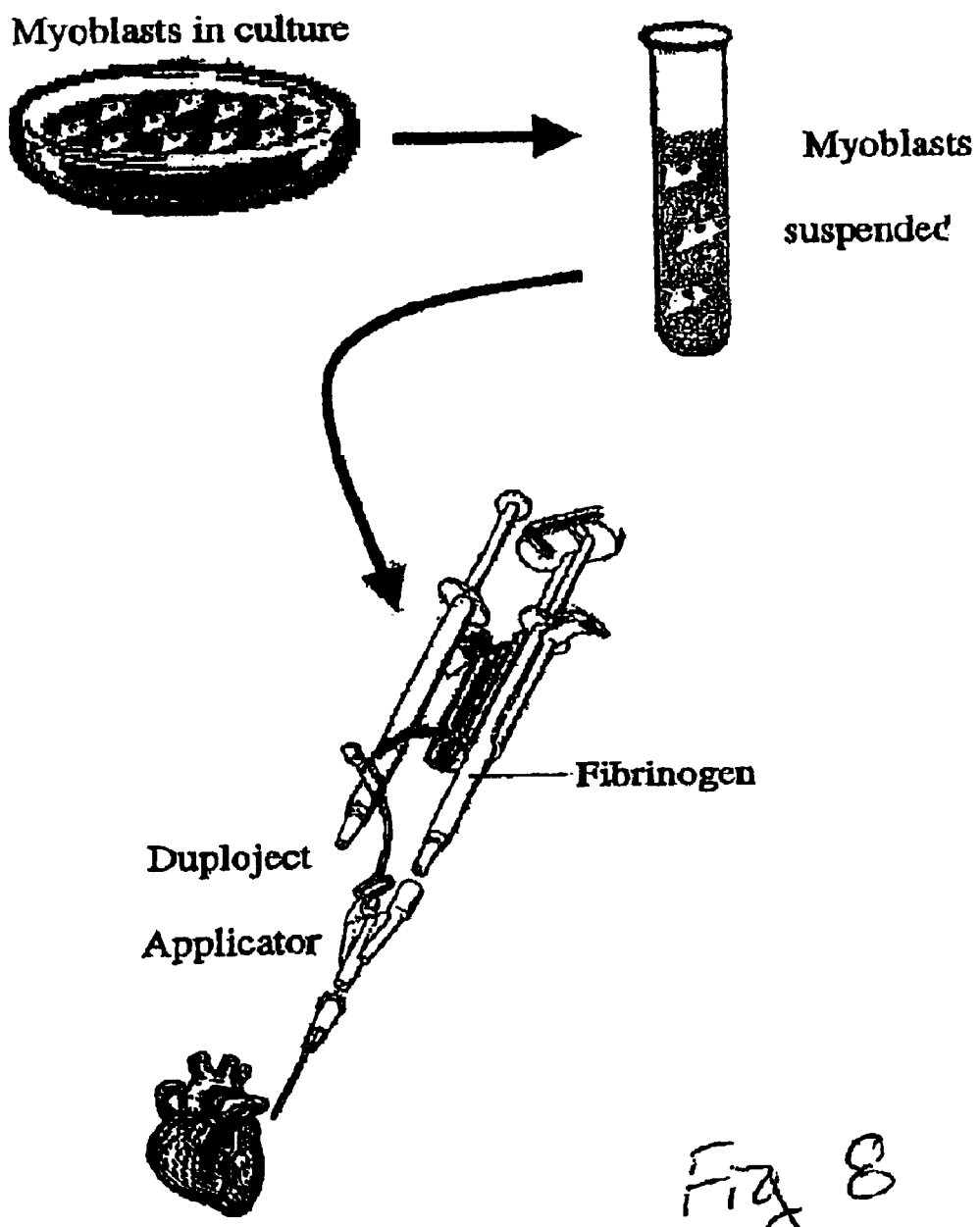
FIG. 8 shows various steps in forming a system for delivering cells in combination with fibrin glue to form a conduction block according to a further embodiment of the invention.

The present invention is useful for treating cardiac arrhythmias as follows by reference to FIGS. 7A–C. More specifically, FIG. 7A shows a region of cardiac tissue 302 that includes an infarct zone 304 that is related to a reentrant conduction pathway 306 (illustrated in bolded arrows) associated with cardiac arrhythmia. As shown in FIG. 7B, the distal end portion 328 of a catheter 320 of the invention is delivered to the region at a location associated with the reentrant circuit 306. This is done for example using a mapping electrode 330 provided at distal tip 329 and via an external mapping/monitoring system 336 coupled to proximal end portion 324 of catheter 320 outside of the body. Needle 340 is punctured into the tissue at the location, and is used to inject non-ablative conduction block material 315 from source 310, also coupled to proximal end portion 324 of catheter 320 outside of the body. According to this highly localized injection of the material 315 into the location across the reentrant circuit 306, the circuit is blocked by material 315 and its arrhythmic effects diminished or entirely remedied with hopeful return to sinus rhythm.

Each type of cardiac arrhythmia is also considered to present unique circumstances, both anatomically and functionally, that may in some circumstances benefit from specially adapted cell delivery devices and techniques in order to provide the most appropriate respective antiarrhythmia therapy.

For example, certain arrhythmias require precisely placed conduction blocks to intervene and block their abnormal conduction. Such circumstances may benefit from specially adapted delivery devices and other considerations such as quantity of cells being delivered.

One illustrative example of a highly beneficial embodiment illustrating such particular adaptation is variously described by reference to the embodiments shown in FIGS. 9A–12 as follows.

Figure 9B:
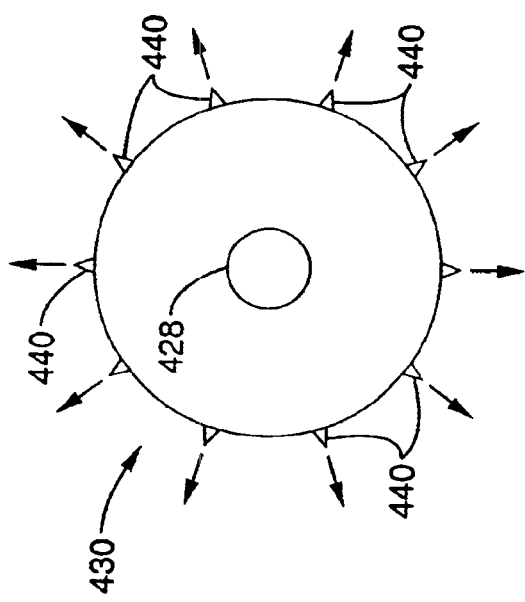
FIG. 9B shows an end view taken along lines B—B in FIG. 9A.
Figure 9A:
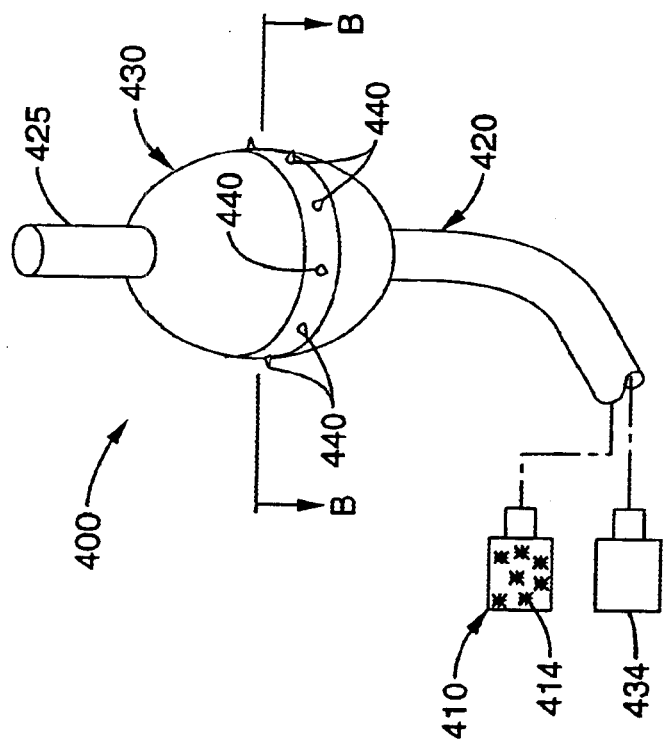
FIG. 9A shows a partially segmented perspective view of a distal end portion of another system according to a further embodiment of the invention.

System 400 shown in FIG. 9A includes a delivery catheter 420 with an expandable member 430 on its distal end portion 428 and coupled to a proximal actuator 434 externally of the body. More specifically, in the embodiment shown expandable member 430 is an inflatable balloon that is coupled via catheter 420 to actuator 434 that is a source of pressurized fluid. A plurality of needles 440 are provided along a circumferential band 436 of balloon 430, as shown in FIG. 9A and also FIG. 9B.

System 400 is in particular adapted for forming non-ablative circumferential conduction block to treat atrial arrhythmia, and still more specifically to form a circumferential conduction block in a circumferential region of tissue at a location where a pulmonary vein extends from an atrium. Such location is generally at a funneling region or ostium 404 between the atrium 402 and respective pulmonary vein 406, but may be located up along the pulmonary vein wall itself to the extent cardiac tissue is located there, and is also considered to include a region of tissue along the back wall of the atrium and closely surrounding the pulmonary vein ostium. All of these regions together may be included in a treatment and be considered at a "location where a pulmonary vein extends from an atrium," or such treatment may be more localized to only one such place, in which case it is still considered a "location where a pulmonary vein extends from an atrium."

In any event, such circumferential conduction block is adapted to substantially isolate cardiac conduction between tissue located on one side of the circumferential region of tissue, e.g. within the circumference, and tissue on the other side, such as outside of circumferential block. In a highly beneficial mode shown in FIG. 10, the balloon 430 is adapted to seat at the location and engage the circumferential region of tissue with the needles 440 penetrating therein. By injecting the material 414 through the needles in a sufficient volume and manner, their injectate will sufficiently inject along the circumference and thereby the circumferential conduction block may be formed.

It is to be appreciated that the conduction block formed by such a device and in similar manner may not be absolute or complete and still provide beneficial results. In one regard, transecting a portion of such a region of tissue may be sufficient to block an arrhythmic conduction path therethrough, such as across "fingers" of cardiac tissue that have been observed to extend up from atria and into the base of pulmonary veins. In addition, such balloon designs that have insufficient needle coverage to provide for overlap between their injectates may be partially rotated one or more times for better circumferential coverage and overlapping. Notwithstanding the foregoing, a complete or substantially complete circumferential conduction block at such pulmonary vein ostial location is considered a highly beneficial embodiment and optimal result in many cases. In fact, by providing such conduction block at such location of each pulmonary vein, atrial fibrillation may be cured without the need for mapping which vessel houses a focal origin of such arrhythmia. While other such procedures using ablation techniques has been previously suggested, by removing the need for ablation according to the present invention, such empirical treatment modality involving all pulmonary veins may become in fact an appropriate choice for AFIB patient care.

Figure 10:
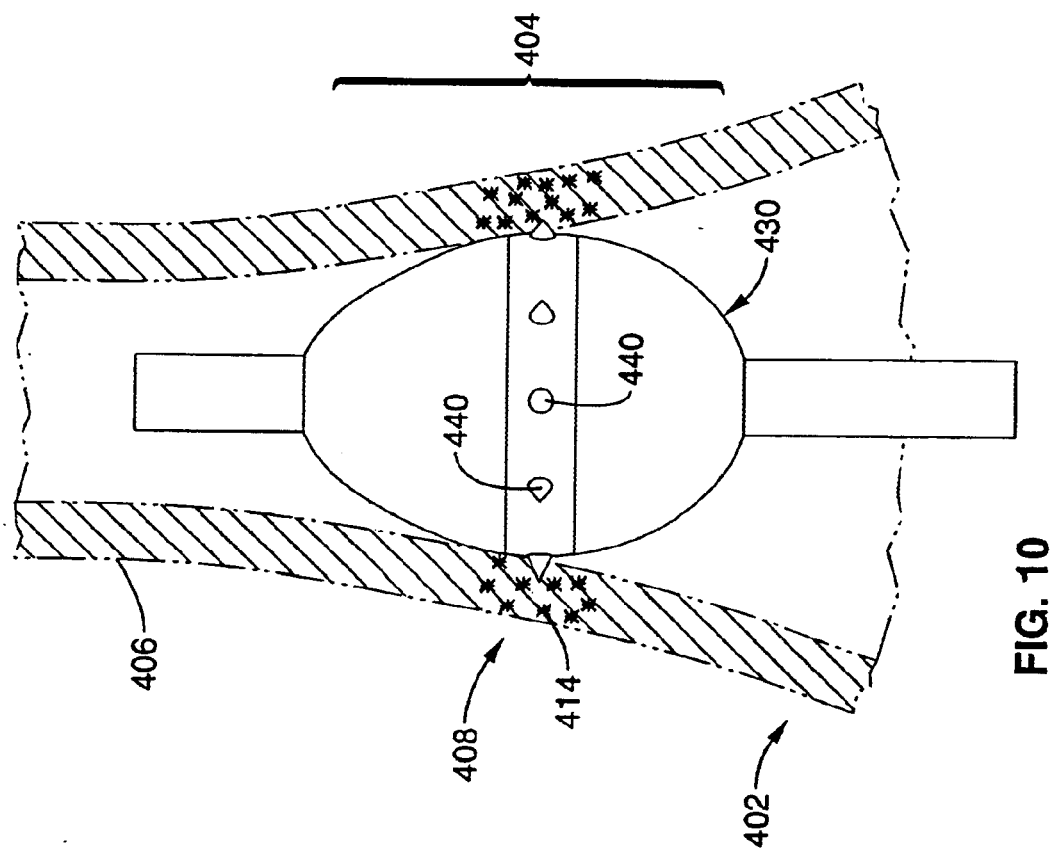
FIG. 10 shows a partially segmented view of a distal end portion of the device shown in FIGS. 9A–B during one mode of in-vivo use at a location where a pulmonary vein extends from an atrium in a patient.
Figure 12:
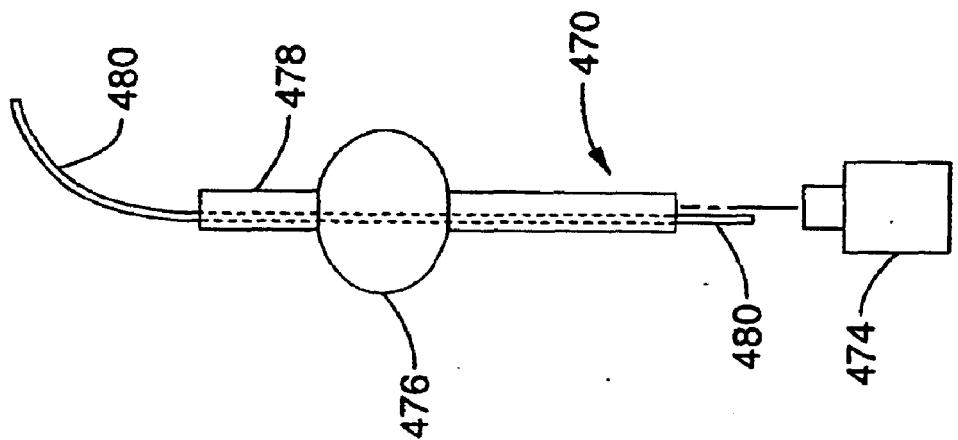
FIG. 12 shows a schematic view of yet another catheter embodiment of the invention.
Figure 11:
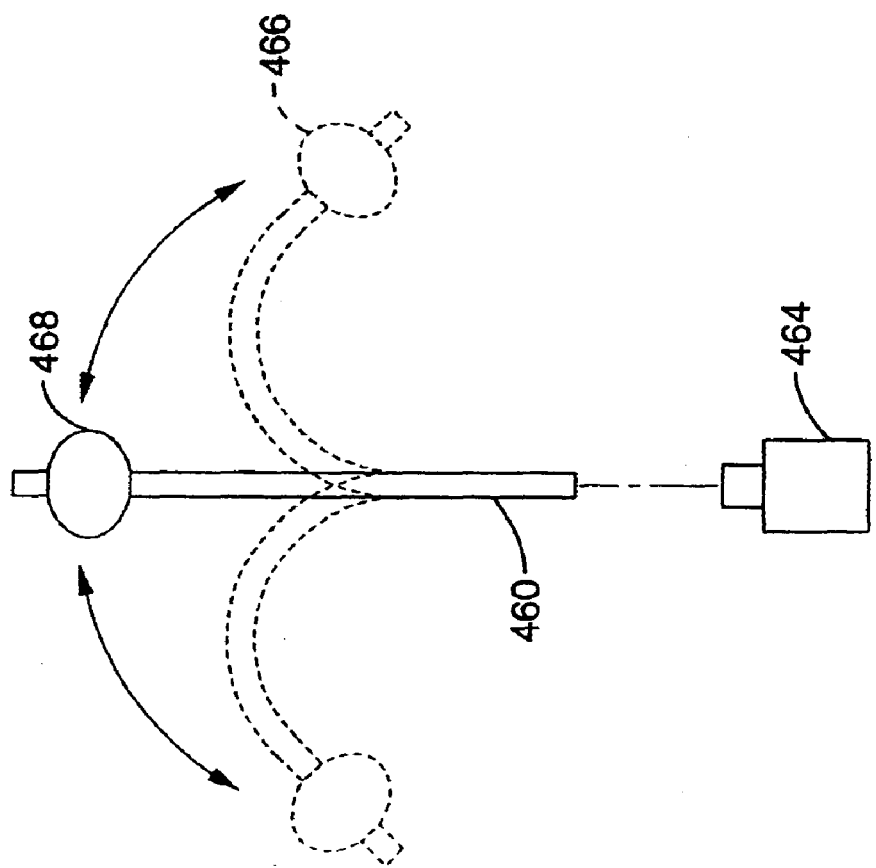
FIG. 11 shows a schematic view of another catheter embodiment according to the invention.
Figure 13B:
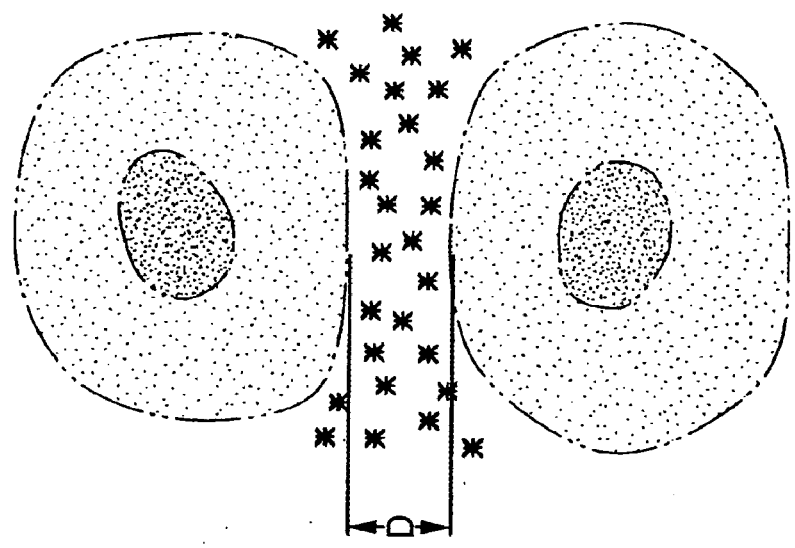
Figure 13A:
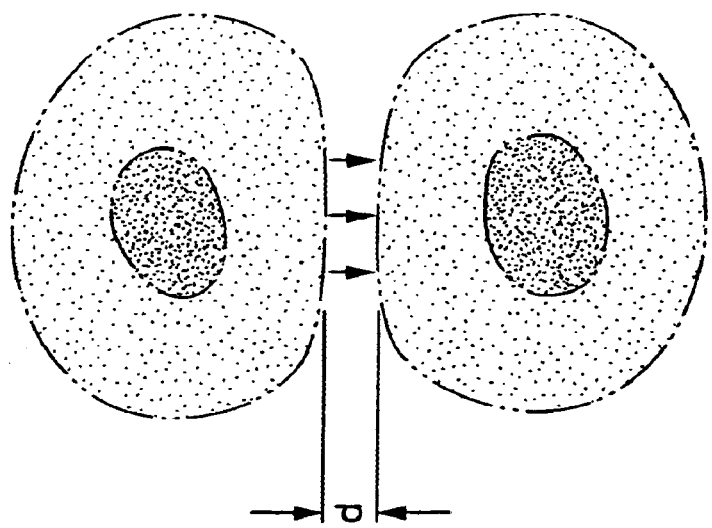

Various further enhancements or modifications of the device just described by reference to FIGS. 9A–10 may be made. For example, a deflectable tip design shown ion FIG. 11 may be used wherein catheter 460 has a distal end portion 468 with a balloon 466 that is deflectable by manipulating actuator 464. Pull wire designs for example may be employed to achieve this embodiment. In another embodiment shown in FIG. 12, a catheter 470 has a guidewire tracking mechanism via an internal lumen that rides over a guidewire 480 so that distal end portion 478 and balloon 476 may be delivered to the pulmonary vein where the guidewire 480 is seated.

In further exemplary modifications, needles may be replaced by other modes for delivering the desired material, such as through walls of porous membranes forming such a circumferential band. Other devices than a balloon may be used as well, such as expandable members such as cages, or other devices such as loop-shaped elongate members that may be configured with appropriate dimension to form the desired circumferential block. Moreover, other blocks than circumferential blocks may be made and still provide benefit without departing from the intended scope hereunder. In one regard, other conduction blocks may be done such as similar to the "maze" procedure and using similar techniques to those previously described using ablation technology.

The present invention has been described above by reference to several highly beneficial embodiments that provide conduction blocks in hearts without substantially ablating cardiac tissue. It is to be appreciated that "without substantially ablating", or terms of similar import, means that the primary mechanism of action is not ablation of tissue, and that the majority of tissue is not ablated at the location of material delivery. However, it is also to be considered that any material being delivered into a tissue may result in some attributable cell death. For example, the pressure of injection, or even the needle penetration itself, may be responsible for killing some cells, but such is not the mechanism by which conduction block is primarily achieved. In a similar regard, at some level it may be the case that all materials have some toxicity to all cells. However, a material is herein considered substantially non-ablative with respect to cardiac cells if such material does not cause substantial ablation as delivered, and cardiac cells can generally survive in the presence of such material in such delivered quantities.

In addition, despite the significant benefit provided according to the various aspects of the invention for non-ablative conduction blocks, further embodiments may also include ablative modes, such as for example by combining cell or fibrin glue delivery with ablation, either concurrently or serially.

Other specialized tools may be made for particular needs related to certain localized arrhythmias. Notwithstanding the substantial benefit that may be gained from such specialized tools and techniques to meet particular needs, such adaptations of cell therapy for treating or preventing cardiac arrhythmias are considered within the broad scope of the present invention.

EXAMPLES

The following is a summary of certain specific examples of experiments that have been conducted and is being provided in order to provide a further understanding of various aspects of the present invention as described by reference to the Summary of the Invention and embodiments described above, and by further reference to the Figures in general.

Example 1

Coupling requirements for successful impulse propagation with skeletal myocytes transplanted in myocardium have been determined by computer modeling as follows in order to determine whether transplanted myocytes can propagate electrical impulses within the myocardium.

The methods according to this example use computer modeling, which constructed theoretical strands of skeletal and mixed skeletal and ventricular myocytes. The ventricular cells were an adaptation of the dynamic Luo Rudy ventricular cell formulation.

Results according to this computer modeling study were as follows. In the mixed strand model, cardiac to skeletal coupling requirements were similar to cardiac-cardiac requirements. In contrast, skeletal to cardiac propagation failed at 300 nS, consistent with the need for a high degree of coupling. According to these results, conditions which decrease intercellular coupling appear to have a marked decrease on transmission between transplanted skeletal cells and the adjoining myocardium. Such effect has been observed to present risk of highly deleterious results when treating hearts in normal sinus rhythm, as the normal propagation of conduction may be dismantled.

However, the present invention contemplates localized use of such transplanted skeletal cells into areas of cardiac cells where conduction is irregular, such as re-entrant arrhythmia pathways. In this unique setting and environment of use, the decreased transmission of conduction arising from injecting cells of this or similar type into the cardiac tissues along such arrhythmia pathways becomes a potent mode for blocking and thus treating such related arrhythmias.

Example 2

To assess the electrophysiologic consequences of skeletal muscle transplantation into the myocardium, an in vivo model was used to assess cardiac conduction. The feasibility of gene transfer to specific areas of the cardiac conduction system has been previously demonstrated (Lee et al. 1198 PACE 21-II: 606; Gallinghouse et al. November 1996 Am Heart Assoc.; U.S. Pat. No. 6,059,726). For example, the highly efficient and specifically localized expression of recombinant beta galactosidase in the AV node of rats and pigs has been described. The accuracy and reproducibility of AV nodal injections has been validated by the production of AV block in rats (Lee et al. 1998 J Appl Physiol. 85(2): 758–763). As an electrically insulated conduit for electrical transmission between the atrium and the ventricle, the AV conduction axis is in a strategic position for the study of cardiac electrophysiology.

To observe the effect of skeletal muscle transplantation on conduction and in particular regarding the electrophysiologic properties of AV nodes, a rat model for AV node injections was utilized (Lee et al. 1998 J Appl Physiol. 85(2): 758–763). Animals were chemically denervated (using atropine and propranolol to inhibit the influence of autonomic nervous system) and studied with right atrial overdrive pacing and atrial programmed extra-stimulation, both pre-injection and at the time of sacrifice. Surface ECG PR intervals were measured, together with AV nodal block cycle length (AVBCL) (the rate at which AV conduction becomes sequentially longer, then fails to conduct) and effective refractory period (ERP) (the coupling interval at which an atrial extrastimulus fails to conduct through the AV node). A single injection of skeletal myoblasts ($1\times10^5$, 15 ul) or vehicle was injected into the AVN of rats (n=8).

Electrophysiologic properties of the AV junction were significantly altered in animals with transplantation of skeletal myoblasts. Significant alterations in the Wenkebach cycle length (70.0±4.4 vs 57.0±5.0 msec; p<0.01) and AV nodal refractory period (113.8±5.6 vs 87.0±6.2 msec; p<0.005) were recorded in the skeletal myoblast injected rats as compared to control animals. Histological examination of the AVN revealed that approximately 10% of the AVN was involved with minimal to no inflammation. Histologically the AV conduction axis appeared normal in control vehicle injections. Interestingly, the PR interval did not significantly change, reflecting the insensitivity of surface EKG markers for cardiac conduction properties.

These results add further evidence that transplanted skeletal myoblasts (even when involving a small portion of the AVN) alters cardiac conduction and may lead to areas of slow conduction or conduction block. Therefore, as the skeletal myoblasts differentiate into myotubes and lose their ability to form gap junctions, the ability to propagate electrical impulses decrease.

Such loss of electrical impulse propagation, e.g. via gap junction loss as just demonstrated in this study, has been previously suggested to represent an adverse outcome to the desired result of treating damaged cardiac tissue via cell therapy by increasing conductivity and/or contractility. In particular with respect to AV node treatments previously posited, such decrease on electrical propagation to the extent of forming conduction blocks has not been previously suggested to be a desired result.

However, the present invention contemplates localized use of such transplanted skeletal cells into areas of cardiac cells where conduction is irregular, such as re-entrant arrhythmia pathways. In this unique setting and environment of use, the decreased transmission of conduction arising from injecting cells of this or similar type into the cardiac tissues along such arrhythmia pathways becomes a potent mode for blocking and thus treating such related arrhythmias.

Example 3

In this study skeletal muscle was chosen as a test form of cell therapy for transplantation into the myocardium in arrhythmic animals to observe for antiarrhythmic effects.

The materials and methods used according to this study were as follows. Neonatal skeletal myoblasts were isolated as previously described by enzymatic dispersion from 2–5 days old Sprague Dawley neonatal rats and cultured as previously described (Rando, T., and Blau, H. M. (1994), J. Cell Biol. 125, 1275–1287). After isolation, cells were cultured with growth medium (GM) (80% F-10 medium (GIBCO BRL), 20% FBS (HyClone Laboratories, Inc.), penicillin G 100 U/ml and streptomycin 100 ug/ml,bFGF 2.5 ng/ml(human, Promega Corp)). Skeletal myoblasts were maintained in GM medium in humidified 95% air and 5% $CO_2$ until used for transplantation.

Sprague-Dawley rats underwent 30 minutes of left coronary artery occlusion and 2 hours of reperfusion. One week following the creation of a myocardial infarction (MI) the rats were divided into two groups. Group 1 (n=7) received two injections (25 ul/injection) of vehicle control (PBS with 0.5% BSA) and Group 2 (n=5) received two injections (25 ul/injection) of rat skeletal myoblasts (total amount of cells: $5\times10^6$). A third group of animals (Group 3) was added. Group 3 animals underwent the transplantation of skeletal myoblasts ($1.5\times10^6$) without an MI. Animals were survived. 5–6 weeks post-MI/cell injection, rats underwent programmed ventricular stimulation and ventricular fibrillation threshold testing. Following the completion of the pacing protocols, rat hearts were harvested for histology.

For this particular illustrative experiment, we use a 30 gauge needle to inject the cells in a single injection via a thoracotamy with direct vision of the heart. The location of injection was based upon results of a previous study, wherein another group of animals underwent 30 minutes of left coronary artery occlusion and 2 hours of reperfusion. After 5–6 weeks, the animals were sacrificed and the hearts isolated and perfused in a Langendorf preparation. Optical mapping was performed which demonstrated a re-entry circuit following the induction of ventricular tachycardia. The location of cell injections for the present study thus was chosen to include the border zone to interrupt such re-entry circuit.

Before sacrifice, ventricular programmed stimulation was performed by applying the pacing electrode on the right ventricle. The pacing protocol consisted of pacing the right ventricle with a train of 8 beats (cycle length of 140 ms) with up to three extra stimuli. Sustained ventricular tachycardia (VT) was defined as VT persisting more than 10 seconds and requiring cardioversion to sinus rhythm. Non-sustained VT (NSVT) was defined as lasting less than 10 seconds and self-limited.

Ventricular fibrillation thresholds (VFT) were obtained by placing the pacing electrode on the right ventricle. Burst pacing (50/sec for 2 sec) was applied and intensified by 0.1 MA each time using a Stimulator (Model DTU, Bloom Associates, LTD, Reading, Pa.). The average threshold of VF from three parts of the right ventricle was used as the electrical intensity which induced VF.

Observation of the test subjects yielded the following results shown in Tables 1 and 2:

TABLE 1

Myoblast Transplantation Effects on VT

|  | NSVT | VT | No VT |
|---|---|---|---|
| Group 1 (MI + vehicle) | 1 | 6 | 0 |
| Group 2 (MI + myoblasts) | 2 | 0 | 3 |
| Group 3 (No MI + myoblasts) | 0 | 0 | 4 |

TABLE 2

Myoblast Transplantation Effects on VFT

|  | VFT (mA) |
|---|---|
| Group 1 (MI + vehicle) | 1.2 ± 0.7 |
| Group 2 (myoblasts) | 3.3 ± 1.8 |

Conduction block was inferentially observed as the optical mapping studies demonstrated a re-entry pattern and the cell delivery prevented sustained VT.

According to the foregoing observations and results of this study, transplantation of skeletal myoblasts into ventricle wall tissue completely prevent sustainable VT in all subjects receiving the cell therapy. In another regard, transplantation of skeletal myoblasts increases the amount of energy required to induce VF versus untreated myocardium. Accordingly, transplantation of myoblasts into cardiac tissue of the ventricle wall provides a potent anti-arrhythmic effect on such tissue. Moreover, the myoblast injections into regions associated with reentry circuits demonstrated anti-arrhythmic effects attributable to conduction block.

The observations, results, and conclusions related to the foregoing study are considered exemplary of cell therapy in general as a potent agent for preventing and treating arrhythmia, and more specifically creating conduction blocks without ablating tissue. Skeletal myoblasts were used as the chosen test sample, and are considered a highly beneficial mode according to the present invention as shown in this study. However, as mentioned above, such use of myoblasts are considered illustrative of a class of cells whose introduction into the cardiac tissue structures intervenes sufficiently to arrhythmic conduction pathways to either create a block or slow the transduction sufficient to reduce the overall effect on sinus rhythm. Such class includes for example other suitable substitute types of cells for providing similar therapy or prophylaxis of cardiac arrhythmias, such as for example stem cells or fibroblasts. Accordingly, in particular with regard to previous cell therapy disclosures intended to primarily increase cardiac conduction such as by modifying activity of cells being delivered, the invention should be considered to broadly encompass cell therapy adapted to block conduction of arrhythmias in tissues associated with cardiac chambers.

Moreover, ventricular arrhythmias were used as the chosen test environment to observe for such anti-arrhythmic effects. Accordingly, a highly beneficial method for treating ventricular arrhythmias, and in particular ventricular fibrillation and tachycardia, has been shown and is considered a beneficial aspect of the invention. However, it is further contemplated that such use is also illustrative of modes for treating arrhythmias in general, and other suitable substitute treatment modalities using cell therapy are contemplated. For example, arrhythmias of either or both ventricles may be treated or prevented using such cell therapy techniques. Still further, atrial arrhythmias such as atrial fibrillation may be treated or prevented. In general, the ability to use cell transplantation to block arrhythmic conduction pathways as illustrated in this present Example is considered applicable to such pathways of any or all the chambers.

Notwithstanding the foregoing, each cell type is considered unique and is therefore believed to provide particular aspects to be accounted for during use.

Example 4

In this study, fibroblasts were chosen as an additional test cell type to observe the effects of their transplantation into cardiac tissue on cardiac arrhythmias.

The purpose of the study is to determine whether fibroblast transplantation into the myocardium effects myocardial remodeling and acts as an anti-arrhythmic agent in preventing ventricular tachycardia.

Dermal fibroblasts were prepared from the skin of fetal Fisher rats. Tissue fragments were digested for 30 minutes in 0.2 U/mL collagenase solution before being plated on collagen-coated dishes in DMEM with 10% FBS and Pen-Strep. The cells were grown at 37° C. in 5% $CO_2$ and passaged upon reaching ~70% confluence, up to the fourth passage. Fibroblasts were selected using a differential adhesion method, where the mixed cell population was incubated for 15 minutes in culture conditions, during which time fibroblasts adhered to the culture plate and myoblasts remained in suspension to be replaced by fresh culture medium.

To verify purity of the fibroblast culture, immunohistochemistry was performed using antibodies to vimentin (1:20 dilution), an intermediate filament present in both myoblasts and fibroblasts, and desmin (1:100 dilution), a muscle-specific protein. Cell suspensions from fibroblast cultures were pipetted into chamber slides and cells were allowed to attach and spread overnight. They were fixed with 2% paraformaldehyde for 5 minutes, then 100% methanol at 0 degrees C. for another 5 minutes. After several PBS rinses and staining buffer blocking, the primary antibodies were added to separate chambers for one hour. (A pure myoblast culture was also used for a positive control for anti-desmin.) Secondary antibodies used were Cy3-conjugated anti-rabbit IgG (1:500 dilution) for the anti-desmin stains, and Cy3-conjugated anti-mouse IgG (1:200 dilution) for the anti-vimentin stains.

Fisher rats were subjected to 30 minutes of left coronary artery occlusion and 2 hours of reperfusion. One week following the creation of a myocardial infarction (MI) the rats were divided into two groups. Group 1 (n=8) received two injections (25 ul/injection) of vehicle control (PBS with 0.5% BSA) and Group 2 (n=8) received two injections (25 $\mu$l/injection) of rat fibroblasts (total amount of cells: $5 \times 10^6$). A dose response was performed with at least 2 other doses of fibroblasts. Fibroblasts were isolated from a skin biopsy, amplified and reinjected into the rat from which the biopsy was taken thus avoiding rejection. Fibroblasts were stained with marker dyes such as CFDA-SE or transfected with B-galactosidase to identify transplanted fibrobalsts from cardiac fibroblasts. A third group of animals (Group 3, n=8) received transplantation of fibroblasts ($1.5 \times 10^6$) without an MI. Animals were survived and underwent echocardiography at week 1 and week 5. 5–6 weeks post-MI/cell injection, rats received programmed ventricular stimulation and ventricular fibrillation threshold testing. Following the completion of the pacing protocols, rat hearts were harvested for histology. MI size and distribution of transplanted fibroblast were determined by histological examination.

Ventricular programmed stimulation was performed by applying the pacing electrode on the right ventricle. The pacing protocol consisted of pacing the right ventricle with a train of 8 beats (cycle length of 140 ms) with up to three extrastimuli. Sustained ventricular tachycardia (VT) was defined as VT persisting more than 10 seconds and requiring cardioversion to sinus rhythm. Non-sustained VT (NSVT) was defined as lasting less than 10 seconds and self-limited.

Ventricular fibrillation thresholds (VFT) were obtained by placing the pacing electrode on the right ventricle. Burst pacing (50/sec for 2 sec) was applied and intensified by 0.1 MA each time using a Stimulator (Model DTU, Bloom Associates, LTD, Reading, Pa.). The average threshold of VF from three parts of the right ventricle were used as the electrical intensity which induced VF.

According to initial results per this protocol above, five (5) rats had no inducible VT, with average ventricular fibrillation threshold equal to 5.5 mA. However, in contrast to previous experiments of the Examples 2–3 above, this study only had 3 control animals which did not have inducible VT. In one regard, in contrast to the other studies above, this study used a different strain of rats.

Despite the absence of a useable control in this study showing unique results between the groups, it is believed that conduction blocks were formed by the fibroblasts in the treatment group rats based upon: (i) the myoblast experience of the prior examples above, (ii) per a further understanding of fibroblast activity as noted above, and (iii) in consideration of the results in this study showing no sustainable VT in treatment group rats. Confirmation of such belief merely requires reproducing such study in a manner yielding a better control (e.g. in a different animal strain).

Example 5

In this study, the effects of injecting fibrin glue, an injectable biopolymer, into cardiac tissue structures were examined, with particular respect to providing an internal support and scaffold and whether it could improve cardiac function and increase infarct wall thickness following MI. Based upon such observations, further use in forming conduction blocks was explored.

A previously described rat ischemia reperfusion model was used in this study. Female Sprague-Dawley Rats (225–250 g) were anesthetized with ketamine (90 mg/kg) and xylazine (10 mg/kg). Under sterile technique, the rats were placed in supine position and the chest was cleaned and shaved. The chest was opened by performing a median sternotomy. Keeping the landmarks of the base of the left atrium and the interventricular groove in view, a single stitch of 7-0 Ticron suture was placed through the myocardium at a depth slightly greater than the perceived level of the left anterior descending portion (LAD) of the left coronary artery while taking care not to enter the ventricular chamber. The suture was tightened to occlude the LAD for 17 minutes and then removed to allow for reperfusion. The chest was then closed and the animal was allowed to recover for 1 week.

Myoblasts from the hind limb muscle of Sprague-Dawley neonatal rats (2–5 days old) were isolated and purified according to the following described procedure. Briefly, the hind limb was harvested under Phosphate buffered saline (PBS)-Penicillin/Streptomycin (PCN/Strep) and mechanically minced. The tissue was enzymatically dissociated with dispase and collagenase (Worthington) in Dulbecco's PBS (Sigma) for 45 minutes at 37° C. The resulting suspension was then passed through an 80 $\mu$m filter and the cells were collected by centrifugation. The cells were preplated for 10 minutes in order to isolate myoblasts from fibroblasts. The myoblast suspension was transferred to a collagen coated 100 mm polystyrene tissue culture dish (Corning Inc) and allowed to proliferate in growth media (80% Ham's F10C media, 20% fetal bovine serum, 1% PCN/Strep, 2.5 ng/ml recombinant human basic fibroblast growth factor) at 37° C. in a humidified atmosphere of 95% air plus 5% $CO_2$. Cultures were allowed to reach a confluency of 70–75% and passaged every 3–4 days (1:4 split).

The fibrin glue used in this study was the commercially available Tisseel VH fibrin sealant (commercially available from Baxter). It is a two component system which remains liquid for several seconds before solidifying into a solid gel matrix. The first component consists of concentrated fibrinogen and aprotinin, a fibrinolysis inhibitor. The second is a mixture of Thrombin and $CaCl_2$. It is delivered through the supplied Duploject applicator, which holds the two components in separate syringes, respectively, and provides simultaneous mixing and delivery (as shown stepwise schematically in FIG. 8). The ratio of fibrinogen to thrombin components was 1:1.

Approximately 1 week after MI, either 0.5% bovine serum albumin (BSA) in 50 microliter PBS (control group), 50 microliter fibrin glue, $5 \times 10^6$ myoblasts in 50 microliter 0.5% BSA, or $5 \times 10^6$ myoblasts in 50 microliters fibrin glue was injected into the ischemic LV. Under sterile technique, the rats were anesthetized and the abdomen was opened from the xiphoid process to a left subaxillar level along the lower rib. The LV apex was exposed via a subdiaphragmatic incision, leaving the chest wall and sternum intact. Rats were randomized to either control or treatment groups and injections were made through a 30-guage needle into the ischemic LV. In the cells group, $5 \times 10^6$ myoblasts were suspended in 50 microliter 0.5% BSA and injected into the myocardium. In the cells in fibrin group, $5 \times 10^6$ myoblasts were suspended in 25 microliter of the thrombin component of the fibrin glue. The thrombin-cell mixture was simultaneously injected into the myocardium with 25 microliter of the fibrinogen component (FIG. 8). 25 microliter thrombin and 25 microliter fibrinogen was simultaneously injected into ischemic myocardium in the fibrin group. The diaphragm was sutured closed after suction of the chest cavity and the abdomen was subsequently closed.

Transthoracic echocardiography was performed on all animals in conscious state approximately one week after MI (baseline echocardiogram), followed by control or treatment injections 1–2 days later. Then a follow-up echocardiogram was performed approximately 4 weeks later. The methodology of echocardiography used in this laboratory has been previously described. Other reports have demonstrated the accuracy and reproducibility of transthoracic echocardiography in rats with myocardial infarcts.

Briefly, the animals were shaved and placed in plastic DecapiCone restrainers (Braintree Scientific Inc.) in conscious state. A layer of acoustic coupling gel was applied to the thorax. Then the animal was placed in a prone or slightly lateral decubitus position. Echocardiography was performed using a 15-MHz linear array transducer system (Acuson Sequoia c256, Mountain View, Calif.). Care was taken to avoid excessive pressure on thorax, which could induce bradycardia. Two-dimensional images were obtained in both parasternal long and short axis views (at the papillary muscle level). Enhanced resolution imaging function (RES) was activated with a region of interest adjusted to heart size whenever possible. The gain was set for best imaging, and the compression was set at 70 dB. The images were acquired digitally and stored on magneto-optical disk (SONY EDM-230C).

Two criteria were used for imaging according to this particular experiment model. First, the short-axis view was given the criteria to demonstrate at least 80% of the endocardial and epicardial border. Second, the long-axis view was given the criteria to demonstrate the plane of mitral valve, where the annulus and the apex could be visualized. After adequate two-dimensional images were obtained, the M-mode cursor was positioned perpendicular to the ventricular anteroseptal wall (at the site of infarct) and the posterior wall, at the level of the papillary muscles. Wall thickness and left ventricular internal dimensions were measured according to the leading edge method of the American Society of Echocardiography. Fractional shortening (FS) as a measure of systolic function was calculated as FS (%)= [(LVIDd−LVIDs)/LVIDd]×100%, where LVID was the left ventricular internal dimension, d was diastole and s was systole. An echocardiographer blinded to the treatment group acquired the images and performed the data analysis. The accuracy and reproducibility of the technique have been reported in a previous study from this laboratory.

Approximately 4 weeks following the injection surgeries, the rats were euthanized with a pentobarbital overdose (200 mg/kg). The hearts were rapidly excised and fresh frozen in Tissue Tek O.C.T. freezing medium. They were then sectioned into 5 micron slices and stained with hematoxylin and eosin (H&E). A subset of hearts from the cells group and cells in fibrin glue group were stained with the MY-32 clone (Sigma), which is directed against the skeletal fast isoform of myosin heavy chain (MHC), in order to label transplanted cells. A Cy-3 conjugated anti-mouse secondary antibody (Sigma) was used to visualize labeled cells. One 250 microliter sample of fibrin glue was also fresh frozen, sectioned into 5 micron slices and stained with H&E.

Data is presented as mean±standard deviation. The rat myocardial infarction model has been generally observed to have a high degree of variability, thus internal controls are implemented in order to evaluate treatment effects. Differences of fractional shortening and infarct wall thickness between measurements before and after injection were compared using a 2 tailed paired t test. Such differences were compared across treatment group using a one-way ANOVA with Bonferroni adjustment. Measurements after injection were also compared between groups using a one-way ANOVA with Bonferroni adjustment. Significance was accepted at $P<0.05$.

A total of 41 rats were used in this study. Six rats died during or immediately following the infarct surgery while one rat died during the injection surgery (cells in fibrin glue group). Post-injection surgery, there was 100% survival in all groups. Final echocardiography measurements were performed on 34 rats. The control group (n=7) was injected with 0.5% BSA, the fibrin group (n=6) was injected with fibrin glue, the cells group (n=6) was injected with $5 \times 10^6$ myoblasts, and the cells in fibrin group (n=5) was injected with $5 \times 10^6$ myoblasts in fibrin glue.

Echocardiography measurements were collected approximately one week post-MI (prior to injection surgery) and approximately four weeks following the injection surgery in order to determine the effects of fibrin glue, myoblasts, and a combination of the two on LV function and infarct wall thickness. As typical of post-MI progression, the control group exhibited a deterioration of LV function and thinning of the infarct wall. After four weeks there was significant deterioration in FS(P=0.0005) as well as a significant decrease in infarct wall thickness (P=0.02) (Table, control group).

In contrast, injection of fibrin glue alone, myoblasts alone, and myoblasts in fibrin glue resulted in the preservation of FS and infarct wall thickness. FS for the fibrin group, cells group, and cells in fibrin group did not significantly decrease by P-values of 0.18, 0.89, and 0.19 respectively (Table). In addition, there was no significant difference in infarct wall thickness for all treatment groups (P=0.40, 0.44, 0.43 respectively) (Table). Differences between before injection and post-injection FS and infarct wall thickness were compared among treatment groups. No significant difference was observed (P=0.52 and P=0.56 respectively), thus indicating that no single treatment was more effective than the others. A comparison of infarct wall thickness among all groups four weeks after injection demonstrates that the wall thickness of the cells in fibrin group is statistically greater than the control (P=0.009) and fibrin groups (P=0.04); however, due to the high degree of variability among infarcts as previously stated, it is more meaningful to use data comparing internal controls.

Fibrin glue is generally observed to form a fibril and porous structure containing fibrils and pores having diameter greater than 2 microns, and is generally termed a coarse gel. Examination of H&E stained heart sections revealed extensive transmural MIs in all groups. In the infarct region, native cardiomyocytes were replaced by fibrillar collagenous scar tissue. At four weeks after injection, the fibrin glue was completely degraded and not visible. Immunostaining for skeletal fast MHC demonstrated that transplanted cells in both the cells group and cells in fibrin group were viable four weeks post-injection and distributed throughout the infarct scar. The transplanted myoblasts in the infarct wall of a heart that was injected with myoblasts in fibrin glue were observed to be aligned in a parallel orientation.

Additionally, cell survival within the infarcted myocardium was enhanced. The mean area covered by transplanted myoblasts was significantly greater when injected in the fibrin scaffold compared to injection in BSA (P=0.02). The myoblast area for cells injected in fibrin glue was $2.8 \pm 0.9$ mm$^2$ while the area for cells injected in BSA was $1.4 \pm 0.5$ mm$^2$. Transplanted myoblasts injected in BSA were most often found at the border of the infarct scar and not within the ischemic tissue. In contrast, myoblasts injected in fibrin glue were found both at the border and within the infarct scar. Cells transplanted in fibrin glue were often surrounding arterioles within the infarct scar.

Fibrin glue, though highly beneficial according to the embodiments of the study herein disclosed, is a biopolymer and thus is illustrative of other materials of similar composition or function in the environment of use that may be suitable substitutes, e.g. other biopolymers.

Fibrin glue is formed by the addition of thrombin to fibrinogen. Thrombin enzymatically cleaves fibrinogen which alters the charge and conformation of the molecule, forming a fibrin monomer. The fibrin monomers then proceed to aggregate forming the biopolymer fibrin. Fibrin is highly involved in wound healing in the body and in conjunction with platelets, is the basis of a clot. No adverse reactions were observed upon injection into the myocardium, including no delivery of clot to or from the heart. Fibrin is resorbed by enzymatic and phagocytic pathways, thus it was expected that no traces of fibrin would remain four weeks post-injection.

The results of the present study indicate that fibrin glue is useful as a support and/or tissue engineering scaffold to prevent LV remodeling and improve cardiac function following MI. Injection of fibrin glue alone as well as injection of skeletal myoblasts in fibrin glue attenuated any decrease in infarct wall thickness and fractional shortening following MI in rats. In accordance with other studies, we also found that injection of skeletal myoblasts alone was able to prevent negative remodeling of the infarcted LV and deterioration of LV function. Although the exact mechanism by which myoblasts preserve LV function is unknown, it is unlikely that it is from active force generation during systole since implanted myoblasts do not form gap junction with surrounding cardiomyocytes. It is believed that the attenuation of negative left ventricular remodeling by the myoblasts is the mechanism that preserves cardiac function. The myoblasts may serve as a wall support by increasing stiffness, or may simply affect remodeling by increasing wall thickness. The data according to this study further supports this. Injection of fibrin glue alone did not produce statistically different results from the injection of skeletal myoblasts, thus suggesting that the mechanism of action of the myoblasts is by preserving wall thickness and preventing deleterious ventricular remodeling, not from active force generation.

A recent study disclosed use of a polymer mesh for the intended purpose of acting as an external support to prevent LV dilation. Fibrin glue may act as an internal support to preserve cardiac function. During the initial stage in MI, matrix metalloproteases are upregulated which results in degradation of the extracellular matrix (ECM). This ECM degradation leads to weakening of the infarct wall and slippage of the myocytes leading to LV aneurysm. In addition, it has been disclosed that negative ventricular remodeling continues until the tensile strength of the collagen scar strengthens the infarct wall. By administering fibrin glue during the initial stage of an infarct, it may prevent remodeling by increasing the mechanical strength of the infarct before the collagen scar has had to time to fully develop. Furthermore, fibrin glue adheres to various substrates including collagen and cell surface receptors (predominately integrins) through covalent bonds, hydrogen and other electrostatic bonds, and mechanical interlocking. Therefore, it may prevent myocyte slippage and subsequent aneurysm by binding to the neighboring normal myocardium. Finally, injection of fibrin glue is also believed to result in an upregulation or release of certain growth factors such as angiogenic growth factors which may improve cardiac function.

In addition to providing an internal support, according to the data of this study it is believed that fibrin is useful as a tissue engineering scaffold in the myocardium. Injection of myoblasts in fibrin glue prevented infarct wall thinning and preserved cardiac function. The wall thickness of this group was also significantly greater than that of other groups. Several previous publications have disclosed delivering a variety of cell types including keratinocytes, fibroblasts, chondrocytes, urothelial cells, and corneal epithelial cells in a fibrin glue scaffold. The results according to the present study also indicate that fibrin glue is capable of delivering viable cells to the myocardium. Although it unlikely that unmodified skeletal myoblasts improve contractility, other cell types including fetal cardiomyocytes and adult bone marrow stem cells, which produce gap junctions in recipient hearts, could be delivered to the myocardium in fibrin glue with the aims of improving both contractility and preventing remodeling.

Another previous disclosure used a tissue engineering approach by delivering fetal cardiomyocytes in alginate scaffolds to the surface of the myocardium and reported preservation of cardiac function. Their results were most likely due to the transplantation of fetal cardiomyocytes and not to the external support of the scaffold due to its small size compared to the LV. The benefit of using fibrin glue as a scaffold is that it is injectable, thus requiring only a minimally invasive procedure in humans. In addition, the cells are delivered directly into the infarcted tissue instead of simply on the epicardial surface.

Notwithstanding the foregoing, and despite what specific mechanisms are in particular involved, the compound preparation, systems, and methods herein disclosed are nevertheless clearly shown provide the intended results in treating certain cardiac conditions.

The results according to this study confirm that preparations and uses of fibrin glue according to the present invention provides a beneficial treatment for patients who suffer from MI. The study shows use of an injectable internal support and/or tissue engineering scaffold to prevent deleterious ventricular remodeling and deterioration of cardiac function. As a support, fibrin glue may be modified to tailor its mechanical properties for this particular application, which modifications are contemplated within the scope of the invention. An increase in thrombin or fibrinogen concentration results in an increase in tensile strength and Young's modulus. An increase in fibrinogen concentration will also decrease the degradation rate of the biopolymer. As a tissue engineering scaffold, fibrin glue is also capable of delivering proteins and plasmids and further embodiments contemplated hereunder use such mechanism to deliver both growth factors, either in protein or plasmid form, and cells to the myocardium.

According to the observations and results of the foregoing study, the present invention further contemplates use of fibrin glue agent, either alone or in combination with certain types of cells, as an injectable material for forming conduction block in cardiac tissue.

Figure 13A:
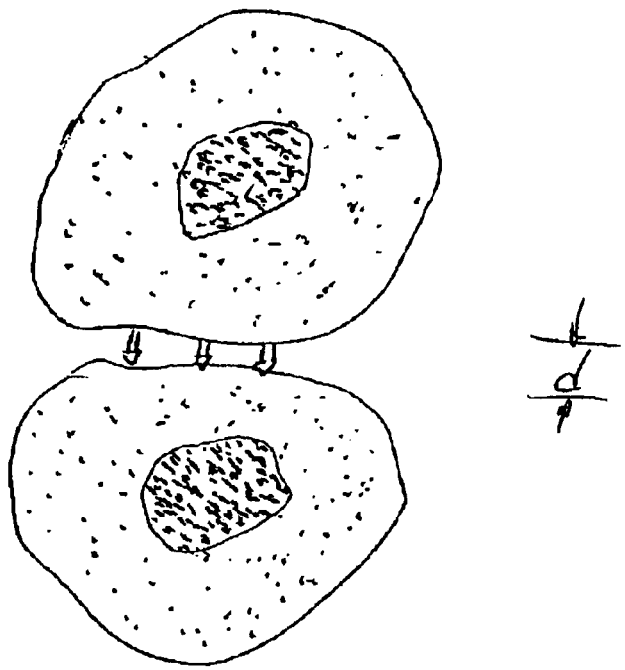
Figure 13B:
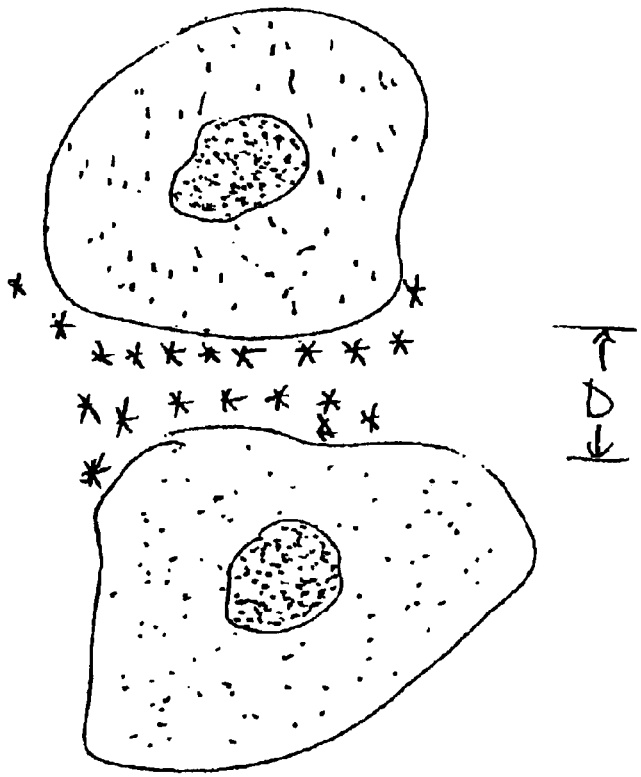

In addition to the mechanisms of action elsewhere herein described, it is further contemplated that injectable materials such as fibrin glue according to the invention may provide conduction block results at least in part by physically separating cells in the region of injection. For further illustration, FIGS. 13A–B show transition between a cellular matrix in an initial gap junction condition (FIG. 13A), and in a post-treatment condition wherein the spacing between cells is physically separated between an initial distance d to a larger, separated distance D (FIG. 13B). These separations may be sufficient to raise the action potential to stimulate conduction between cells to such level that conduction is blocked or otherwise retarded sufficiently to halt arrhythmia.

Notwithstanding certain theories herein posited with respect to the mechanisms by which certain embodiments act, it is to be appreciated that the use of certain materials and procedures to the extent they produce certain intended results are contemplated under the invention despite the actual mechanism by which the results are accomplished.

Various descriptions of materials provided herein may be in particular beneficial, such as for example various references to fibrin glue or related agent, or analogs or derivatives thereof. However, other suitable materials may be used in certain applications, either in combination or as substitutes for such particular materials mentioned. In one particular regard, where fibrin glue or related agents are herein described, it is further contemplated that collagen, or precursors or analogs or derivatives thereof, may also be used in such circumstances, in particular relation to forming conduction blocks or otherwise treating cardiac arrhythmias. Moreover, where collagen is thus included, precursor or analogs or derivatives thereof are further contemplated, such as for example structures that are metabolized or otherwise altered within the body to form collagen, or combination materials that react to form collagen, or material whose molecular structure varies insubstantially to that of collagen such that its activity is substantially similar thereto with respect to the intended uses contemplated herein (e.g. removing or altering non-functional groups with respect to such function). Such group of collagen and such precursors or analogs or derivatives thereof is herein referred to as a "collagen agent."

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for treating a cardiac arrhythmia in a heart of a patient, comprising:

identifying a location for creating a conduction block adapted to treat the cardiac arrhythmia;

providing an injectable material that comprises a collagen agent; and forming a conduction block at the location injecting the collagen agent material to the location and without substantially ablating cardiac cells; and wherein the cardiac arrhythmia is treated by forming the substantially non-ablative conduction block with the injected collagen agent material.

2. The method of claim 1, further comprising: intervening with gap-junctions of cardiac tissue with the collagen agent material.

3. The method of claim 1, wherein the material being delivered to the region further comprises a polymer agent.

4. The method of claim 3, wherein the material being delivered to the region further comprises a second polymer agent.

5. The method of claim 1, wherein the delivery of the material to the location comprises:

mixing first and second precursor collagen agent materials within the body of the patient to form polymerized collagen at the location in situ.

6. The method of claim 1, wherein the material being delivered to the location further comprises living cells.

7. The method of claim 6, wherein the living cells comprise myoblasts.

8. The method of claim 1, wherein the region to which the material is being delivered is located along a ventricular wall of a ventricle of the patient's heart.

9. The method of claim 1, wherein the region to which the material is being delivered is located along an atrial wall of an atrium of the patient's heart.

10. The method of claim 1, further comprising:

injecting the injectable collagen agent into the location from within a cardiac chamber of the patient's heart.

11. The method of claim 1, further comprising:

delivering fibroblast cells to the location where the collagen agent is injected.

12. The method of claim 1, further comprising:

delivering stem cells to the location where the collagen agent is injected.

13. The method of claim 1, wherein the collagen agent material is injected in a manner so as to form a conduction block along a pre-determined pattern.

14. The method of claim 13, wherein the predetermined pattern is adapted to form a substantially circumferential conduction block.

15. The method of claim 13, wherein the predetermined pattern and location are positioned where a pulmonary vein extends from an atrium.

16. The method of claim 1, further comprising:

mapping an electrical conduction signal within the heart;

determining the location based upon the mapped electrical conduction signal; and wherein the mapped electrical conduction signal is associated with the cardiac arrhythmia.

* * * * *

UNITED STATES PATENT AND TRADEMARK OFFICE
CERTIFICATE OF CORRECTION

PATENT NO.      : 6,932,804 B2                                               Page 1 of 12
APPLICATION NO. : 10/349323
DATED           : August 23, 2005
INVENTOR(S)     : Randall J. Lee It is certified that error appears in the above-identified patent and that said Letters Patent is hereby corrected as shown below:

The drawing sheets provided with the issued patent include informal drawings figures. Delete and insert formal drawings (see attached)

Signed and Sealed this

Twenty-fourth Day of October, 2006

JON W. DUDAS
*Director of the United States Patent and Trademark Office*

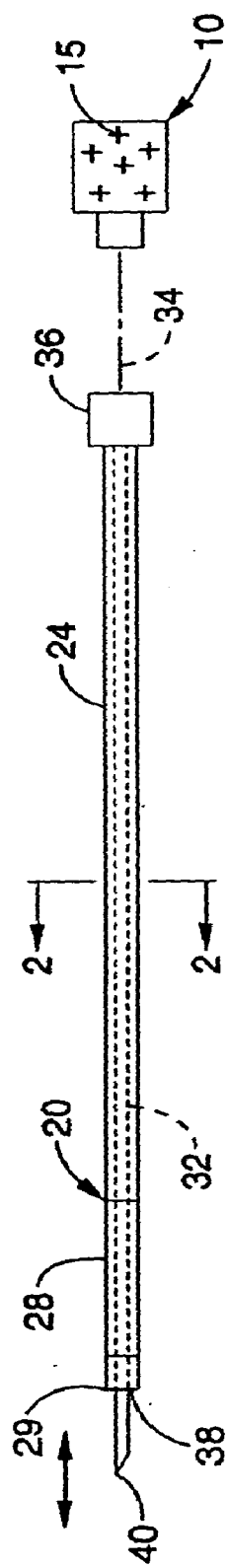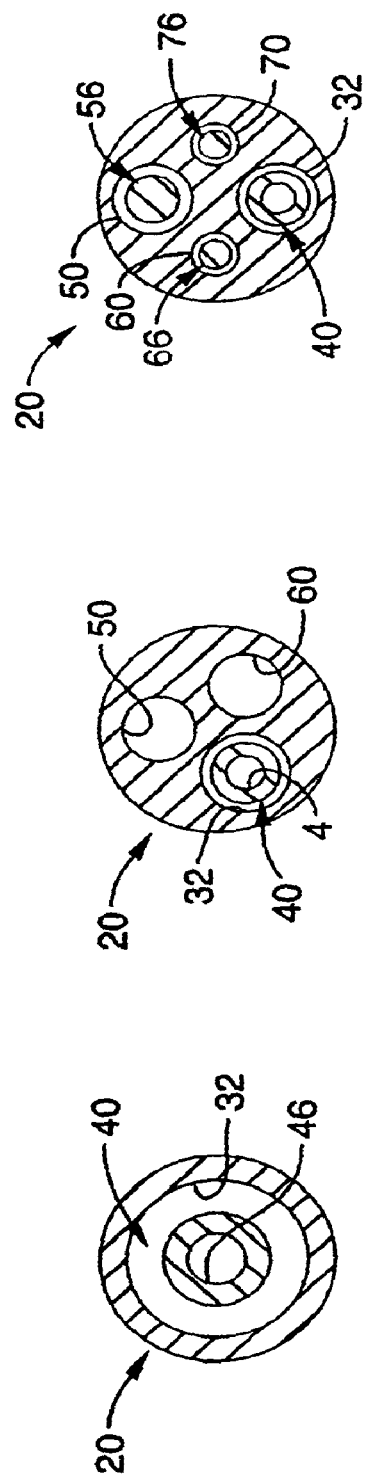

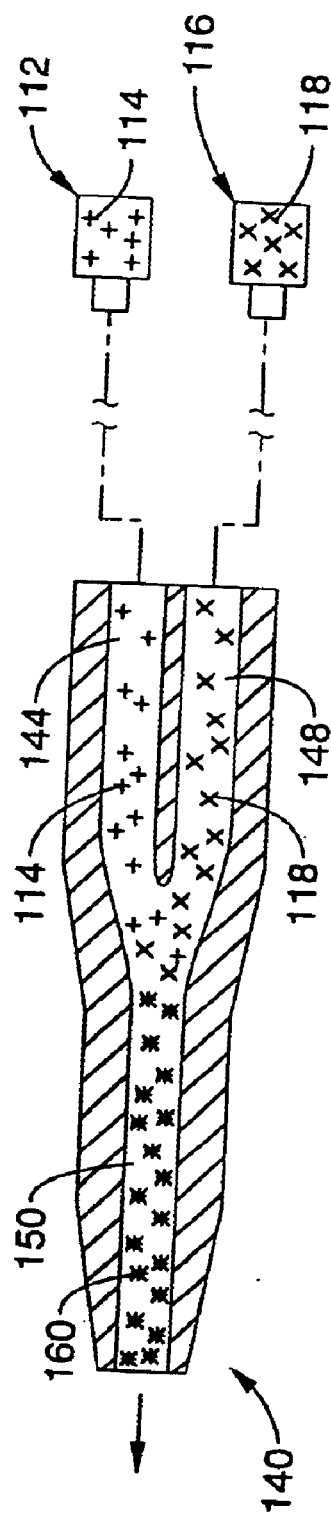
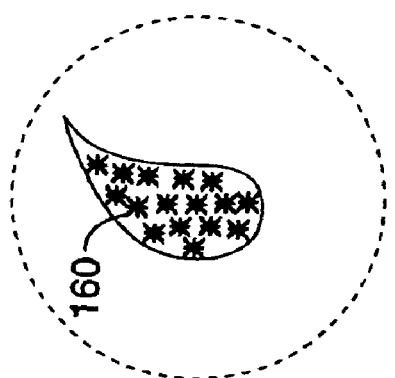
FIG. 4
FIG. 5